United States Patent
Miesel et al.

[11] Patent Number: 6,125,291
[45] Date of Patent: *Sep. 26, 2000

[54] LIGHT BARRIER FOR MEDICAL ELECTRICAL LEAD OXYGEN SENSOR

[75] Inventors: Keith A. Miesel, St. Paul; Eric M. Stetz, Coon Rapids, both of Minn.

[73] Assignee: Medtronic, Inc., Minneapolis, Minn.

[*] Notice: This patent is subject to a terminal disclaimer.

[21] Appl. No.: 09/182,764

[22] Filed: Oct. 30, 1998

[51] Int. Cl.⁷ .................................................. A61N 5/08

[52] U.S. Cl. ............................ 600/333; 600/339; 607/22

[58] Field of Search ................................... 600/322, 323, 600/324, 325, 332, 333, 335, 341; 607/22, 122

[56] References Cited

U.S. PATENT DOCUMENTS

| | | |
|---|---|---|
| H1114 | 12/1992 | Schweitzer et al. |
| 3,746,087 | 7/1973 | Lavering et al. |
| 3,847,483 | 11/1974 | Shaw et al. |
| 4,114,604 | 9/1978 | Shaw et al. |
| 4,202,339 | 5/1980 | Wirtzfeld et al. |
| 4,399,820 | 8/1983 | Wirtzfeld et al. |
| 4,407,296 | 10/1983 | Anderson. |
| 4,421,386 | 12/1983 | Podgorski. |
| 4,444,498 | 4/1984 | Heinemann. |
| 4,467,807 | 8/1984 | Bornzin. |
| 4,523,279 | 6/1985 | Sperinde et al. |
| 4,554,927 | 11/1985 | Fussell. |
| 4,623,248 | 11/1986 | Sperinde. |
| 4,651,741 | 3/1987 | Passafaro. |
| 4,697,593 | 10/1987 | Evans et al. |
| 4,727,879 | 3/1988 | Liess et al. |
| 4,730,389 | 3/1988 | Baudino et al. |
| 4,730,622 | 3/1988 | Cohen. |
| 4,750,495 | 6/1988 | Moore et al. |
| 4,791,935 | 12/1988 | Baudino et al. |
| 4,807,629 | 2/1989 | Baudino et al. |
| 4,807,632 | 2/1989 | Liess et al. |
| 4,813,421 | 3/1989 | Baudino et al. |
| 4,815,469 | 3/1989 | Cohen et al. |
| 4,827,933 | 5/1989 | Koning et al. |
| 4,830,488 | 5/1989 | Heinze et al. |

(List continued on next page.)

FOREIGN PATENT DOCUMENTS

WO 80/01620  8/1980  WIPO.
WO 94/13200  6/1994  WIPO.

OTHER PUBLICATIONS

W. H. Ko et al., "A Design of Capacitive Pressure Transducer," IEEE: New York 1984.

V. Gaeger, R. Kobs and M. Liehr, "A Ceramic Differential–Pressure Transducer," Philips Tech., Rev. 43, S6–93.

J.F. Dias et al., "Capacitive Blood Pressure Transducer," ISA Transactions, vol. 19, No. 3, pp. 19–23, 1980.

Hin–Leung Chau, Member, IEEE, and Kensall D. Wise, Fellow, IEEE, "An Ultraminiature Solid–State Pressure Sensor for a Cardiovascular Catheter," IEEE Trans. Electron Devices, vol. 35, No. 12, pp. 2355–2362, Dec. 1988.

"Capacitive Transducers," Capacitive Gaging System, courtesy of Lion Precision Corp., Newton, Mass. Section 4.1, in part, is from Harry E. Thomas *Handbook of Biomeical Instrumentation and Measurement*, Reston Publishing Co., Reston, Va., 1974, p. 12.

R. V. Jones and J C S Richards, "The Design and Some Applications of Sensitive Capacitance Micrometers," Natural Philosophy Department, Aberdeen University, Aberdeen AB9 2UE, pp. 589–600, 1973.

*Primary Examiner*—Eric F. Winakur
*Attorney, Agent, or Firm*—Thomas F. Woods; Girma Wolde-Michael; Harold R. Patton

[57] ABSTRACT

An implantable sensor assembly for use with an implantable medical device are disclosed. The sensor assembly preferably includes two or more physiologic sensors coupled to the medical device via a pair of lead conductors, or alternatively an oxygen sensor having certain features. The oxygen sensor permits more accurate and reliable measurement of oxygen saturation in blood masses flowing within the human body.

95 Claims, 21 Drawing Sheets

U.S. PATENT DOCUMENTS

| | | |
|---|---|---|
| 4,877,032 | 10/1989 | Heinze et al. . |
| 4,903,701 | 2/1990 | Moore et al. . |
| 4,967,755 | 11/1990 | Pohndorf . |
| 5,005,573 | 4/1991 | Buchanan . |
| 5,040,538 | 8/1991 | Mortazavi . |
| 5,052,388 | 10/1991 | Sivula et al. . |
| 5,058,586 | 10/1991 | Heinze . |
| 5,067,960 | 11/1991 | Grandjean . |
| 5,113,862 | 5/1992 | Mortazavi . |
| 5,113,868 | 5/1992 | Wise et al. . |
| 5,176,138 | 1/1993 | Thacker . |
| 5,199,428 | 4/1993 | Obel et al. . |
| 5,267,564 | 12/1993 | Barcel et al. . |
| 5,275,171 | 1/1994 | Barcel . |
| 5,312,454 | 5/1994 | Roline et al. . |
| 5,324,326 | 6/1994 | Lubin . |
| 5,329,922 | 7/1994 | Atlee, III . |
| 5,342,406 | 8/1994 | Thompson . |
| 5,358,519 | 10/1994 | Grandjean . |
| 5,377,524 | 1/1995 | Wise et al. . |
| 5,411,532 | 5/1995 | Mortazavi . |
| 5,438,987 | 8/1995 | Thacker et al. . |
| 5,490,323 | 2/1996 | Thacker . |
| 5,535,752 | 7/1996 | Halperin et al. . |
| 5,556,421 | 9/1996 | Prutchi et al. . |
| 5,564,434 | 10/1996 | Halperin et al. . |
| 5,593,430 | 1/1997 | Renger . |
| 5,601,611 | 2/1997 | Fayram et al. . |
| 5,730,125 | 3/1998 | Prutchi et al. .......................... 600/323 |
| 5,743,267 | 4/1998 | Nikolic et al. . |
| 5,758,652 | 6/1998 | Nikolic et al. . |
| 5,788,647 | 8/1998 | Eggers . |
| B1 4,467,807 | 6/1992 | Bornzin . |

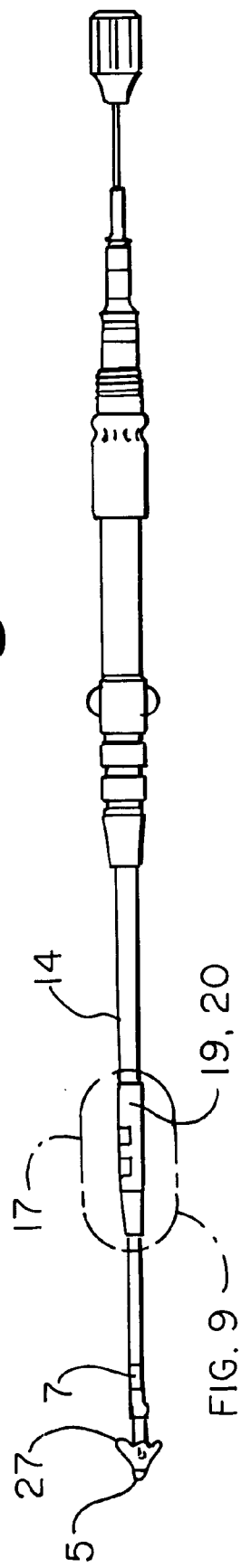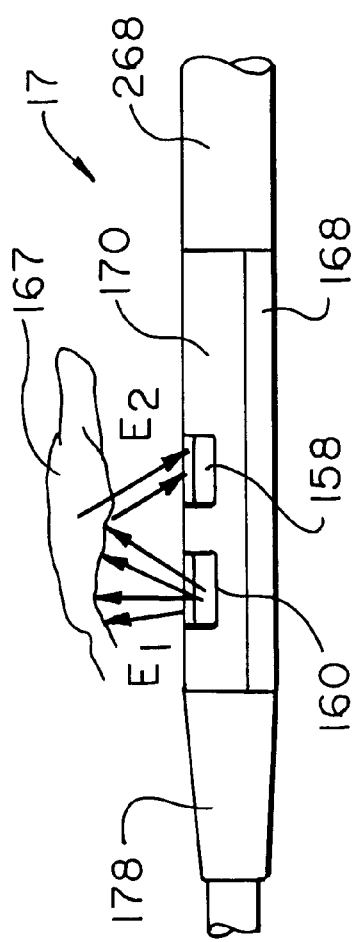

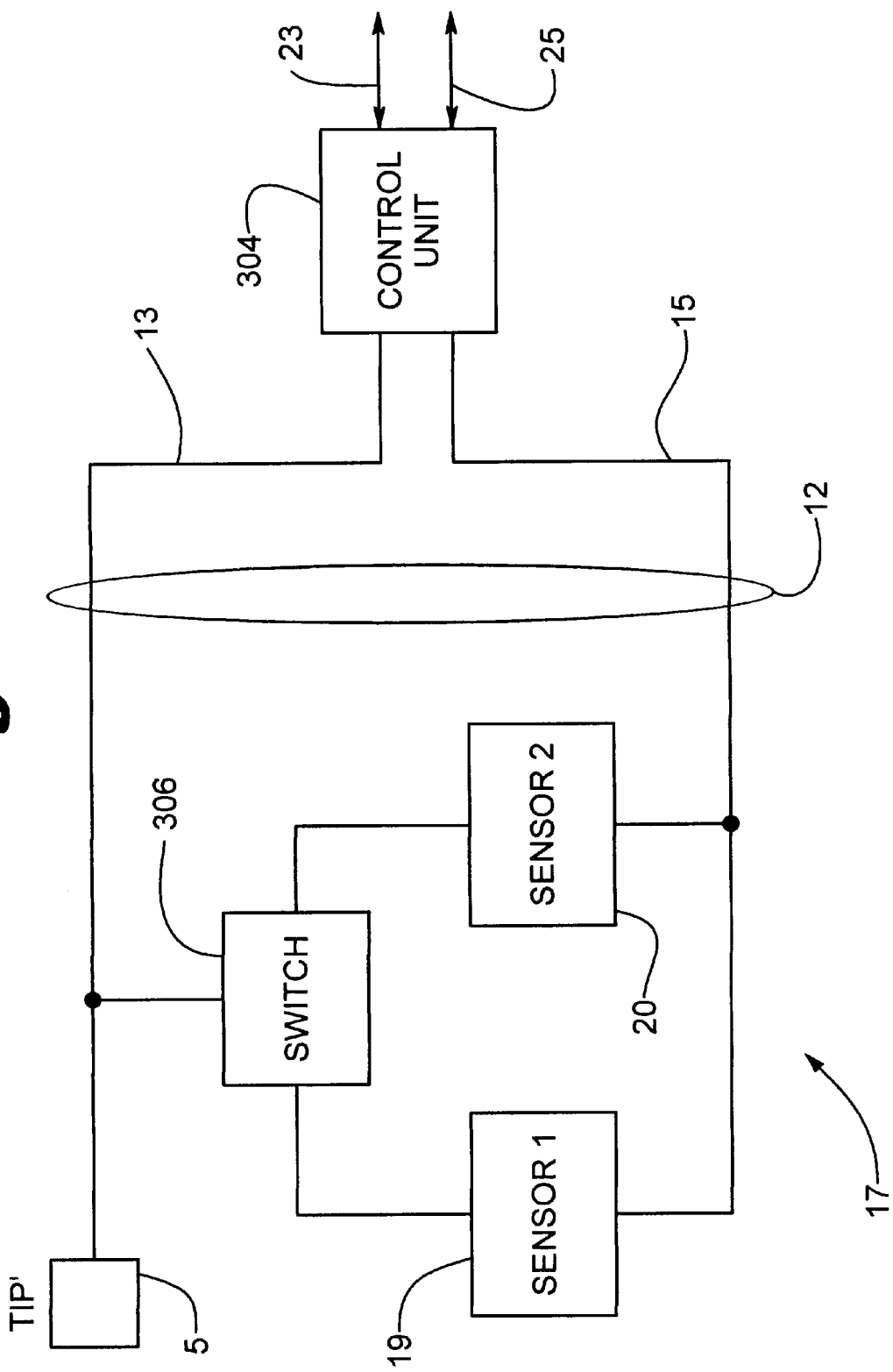

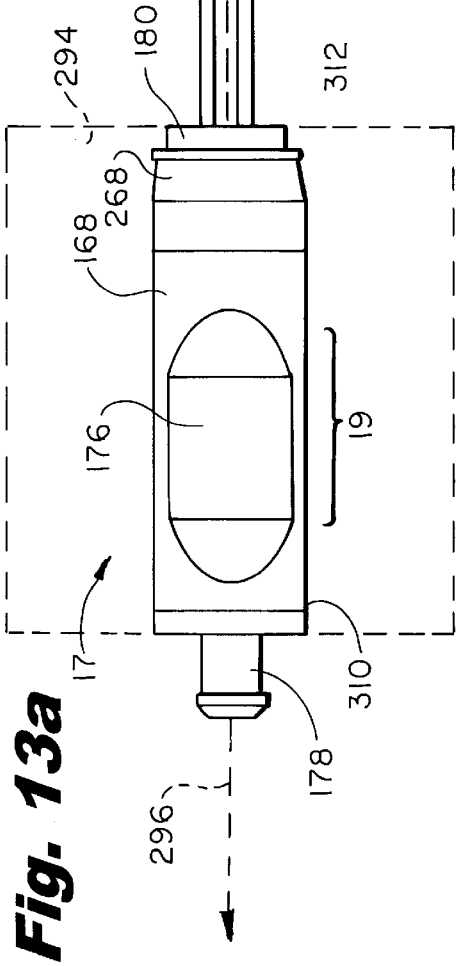
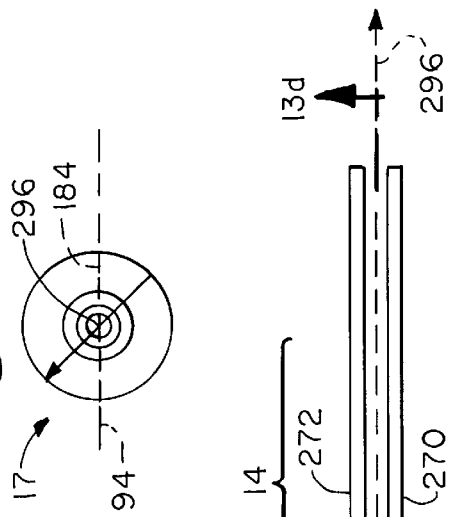
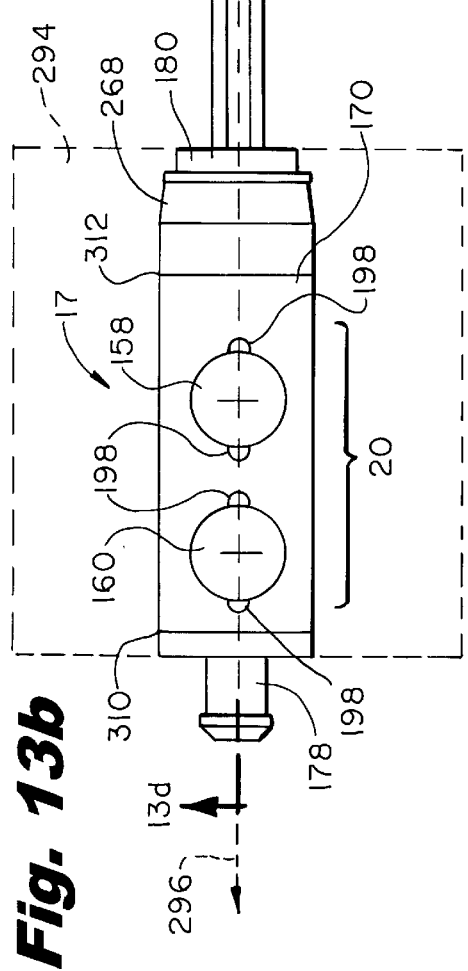

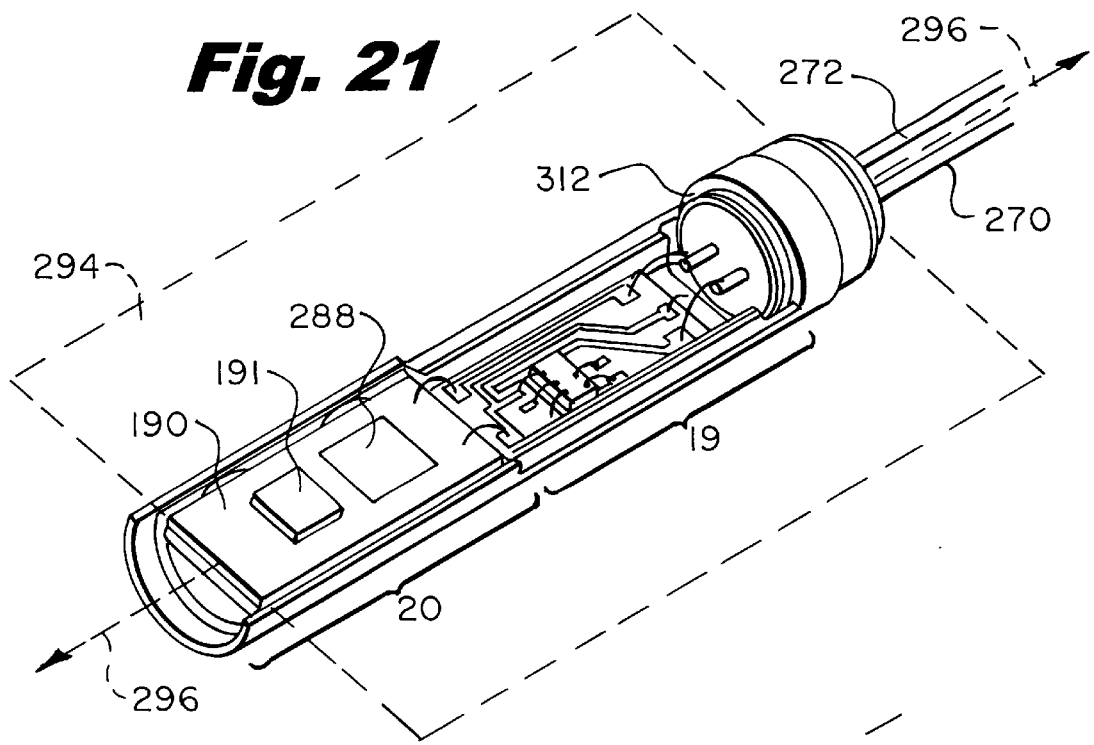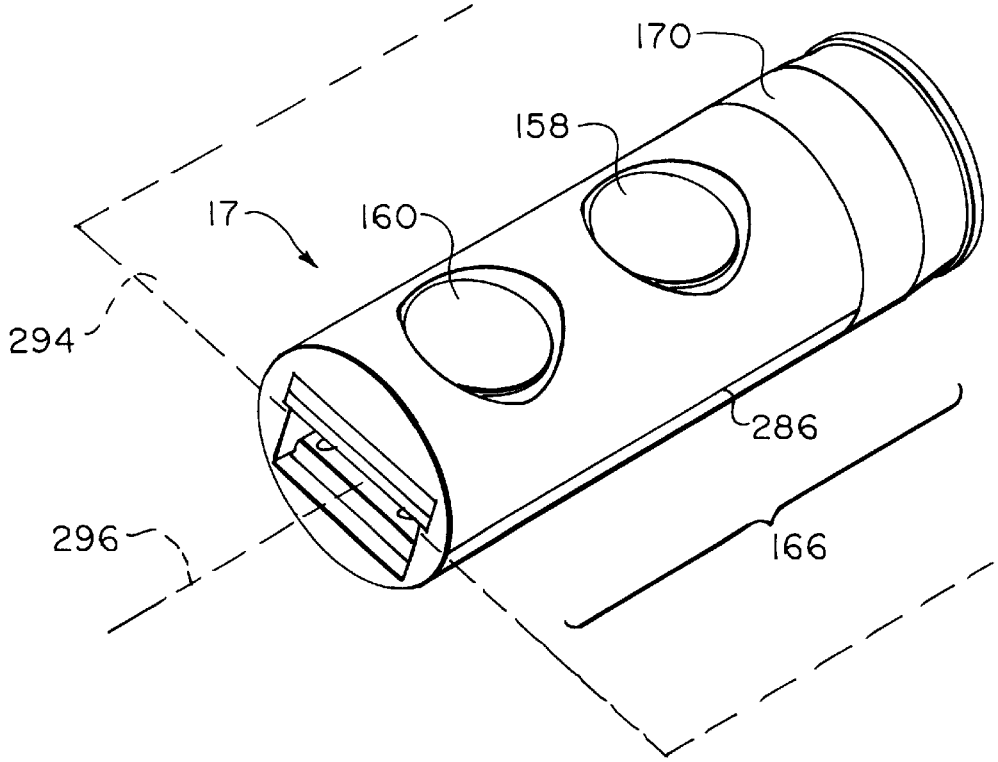

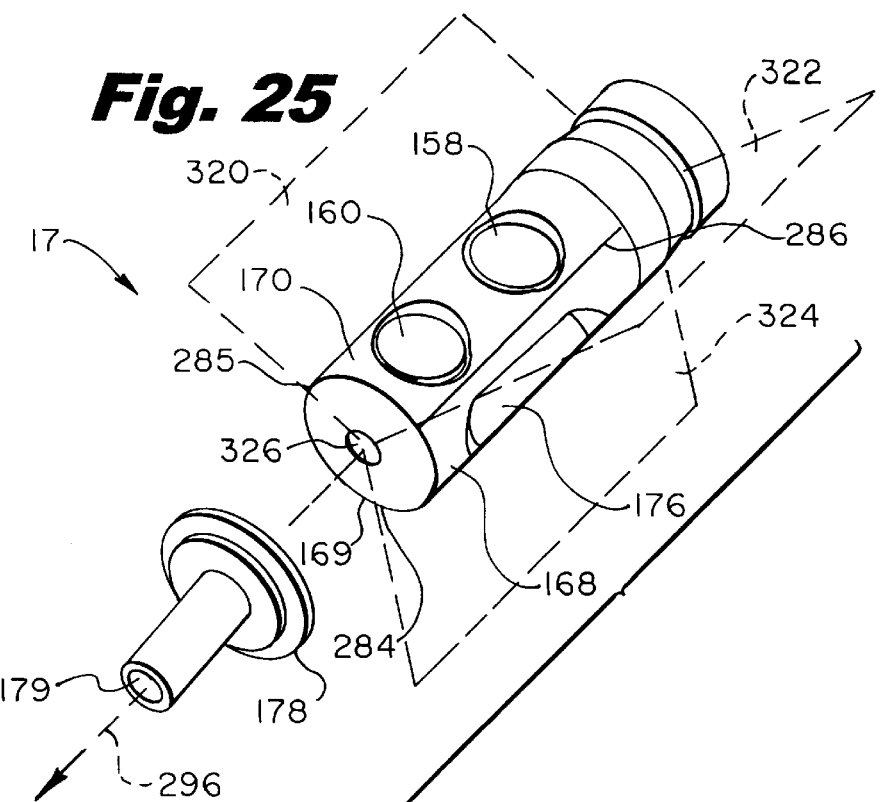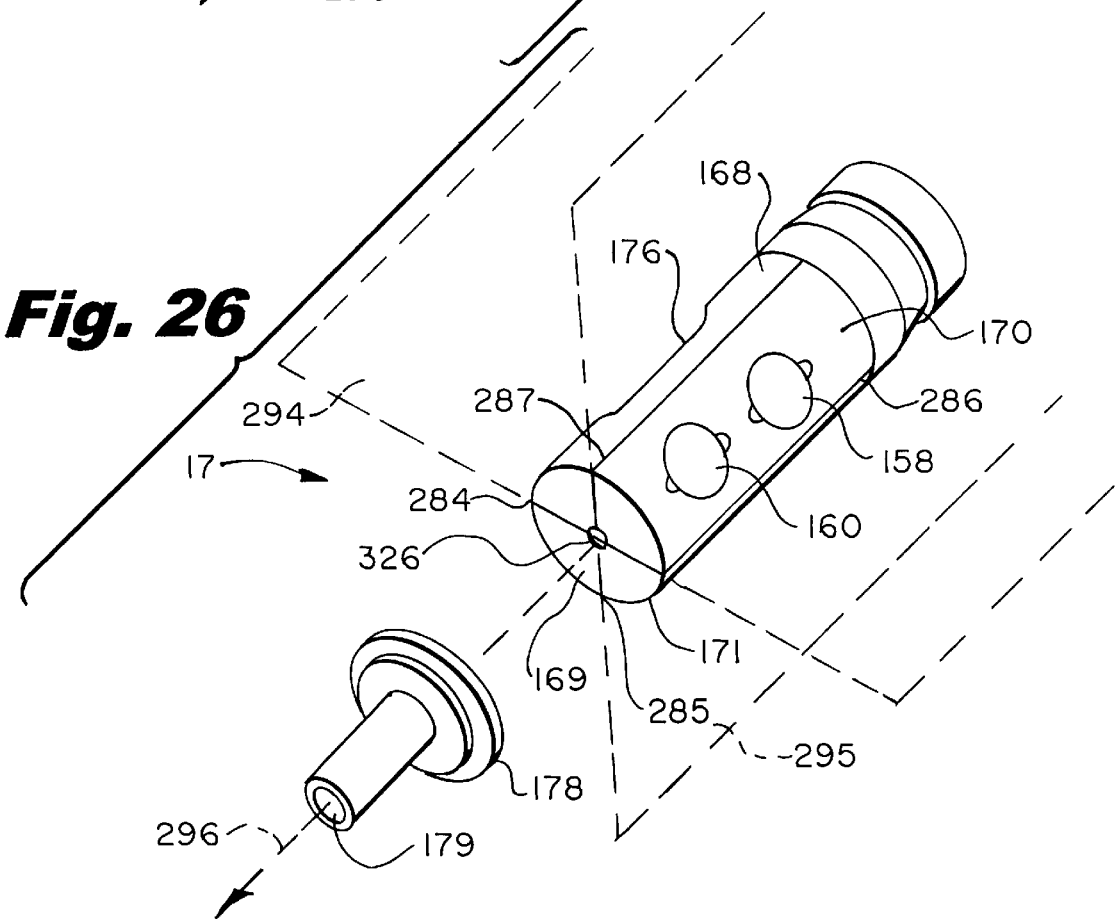

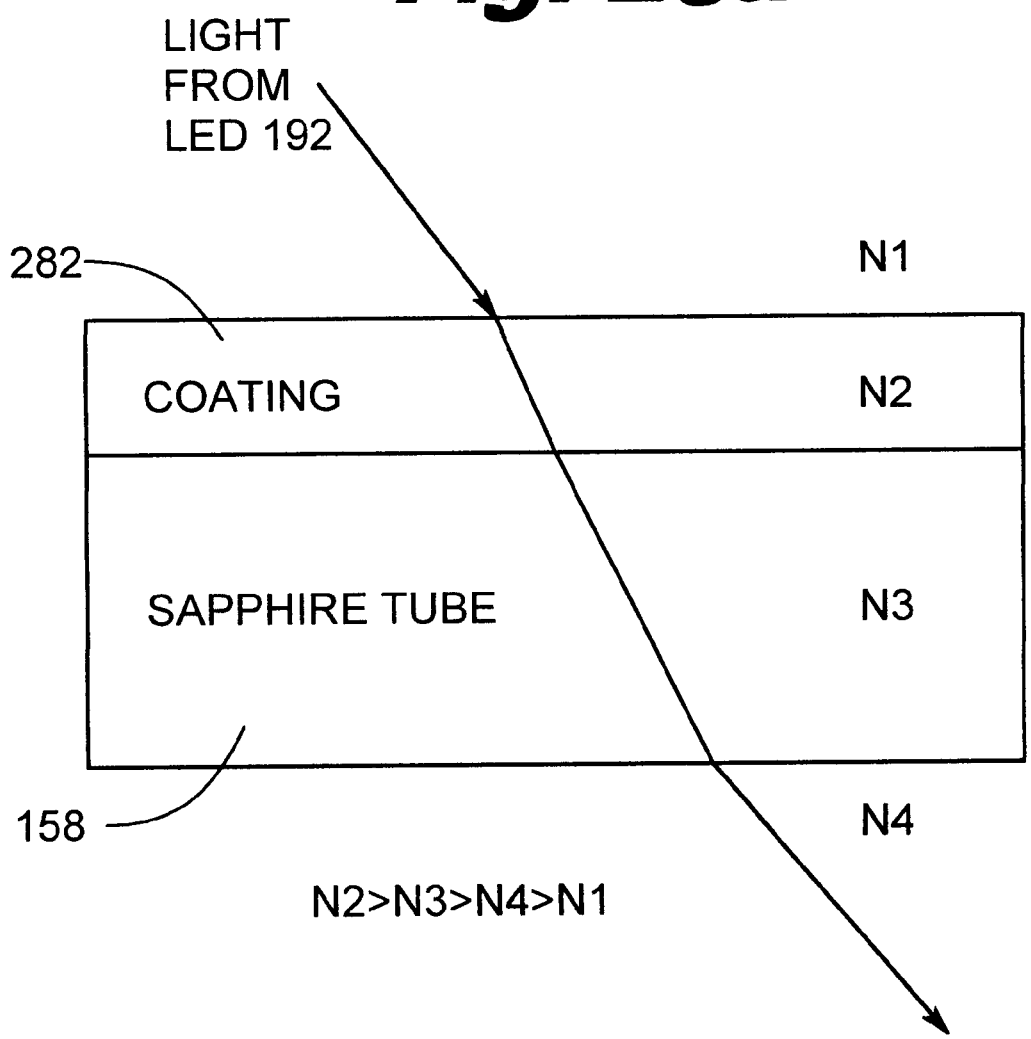

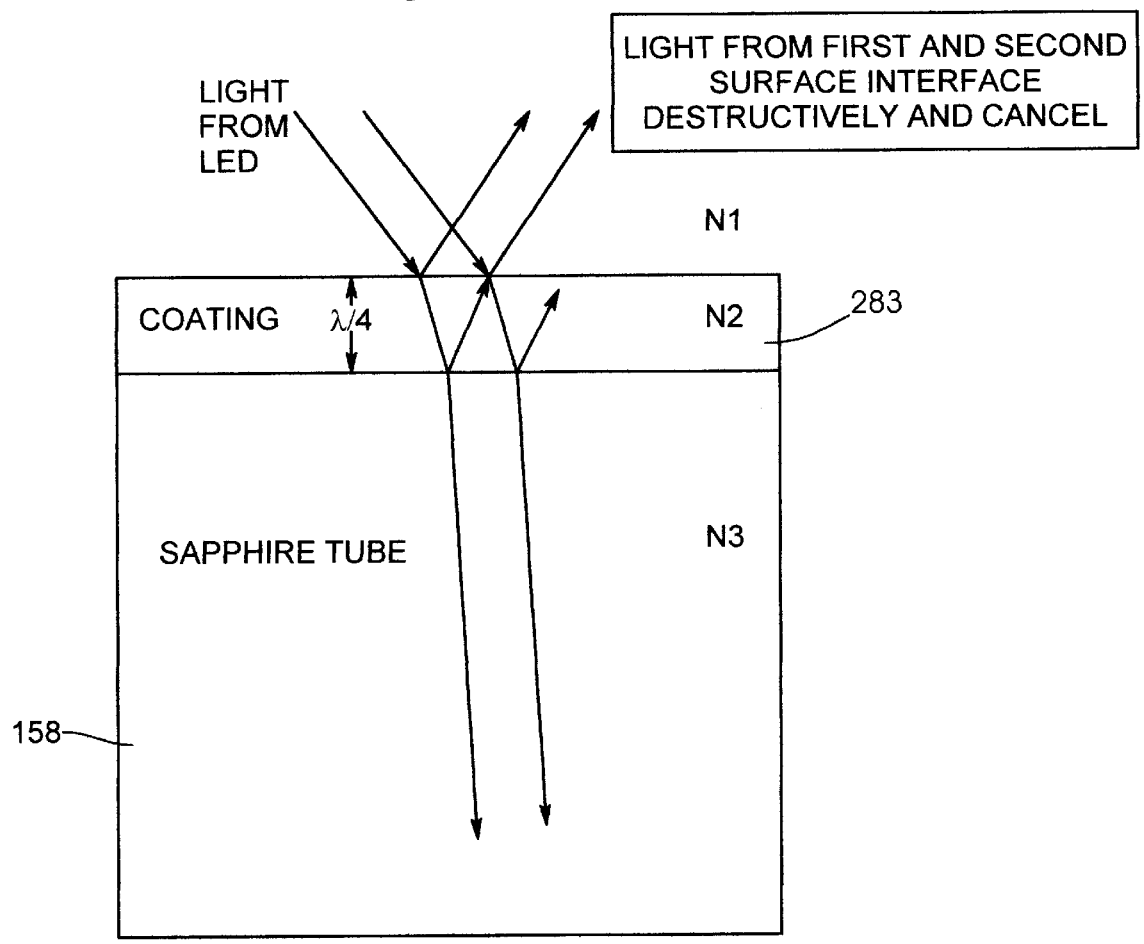

LIGHT BARRIER FOR MEDICAL ELECTRICAL LEAD OXYGEN SENSOR

FIELD OF THE INVENTION

The present invention relates generally to implantable physiologic sensors.

BACKGROUND OF THE INVENTION

Implantable medical devices (IMDs) for cardiac monitoring or for delivering therapy typically include one or more sensors positioned in a patient's blood vessel, heart chamber or other portion of the body. Examples of IMDs include heart monitors, therapy delivery devices, pacemakers, implantable pulse generators (IPGs), pacer-cardio-defibrillators (PCDs), implantable cardio-defibrillators (ICDs), cardiomyo-stimulators, nerve stimulators, gastric stimulators, brain stimulators and drug delivery devices. In a cardiac therapy or monitoring context, such IMDs generally include electrodes for sensing cardiac events of interest and sense amplifiers for recording or filtering sensed events.

In many currently available IMDs, sensed events such as P-waves and R-waves are employed to control the delivery of therapy in accordance with an operating algorithm. Selected electrogram (EGM) signal segments and sense event histogram data and the like are typically stored in IMD RAM for transfer to an external programmer by telemetric means at a later time.

Efforts have also been made to develop implantable physiologic signal transducers and sensors for monitoring a physiologic condition other than, or in addition to, an EGM, to thereby control delivery of a therapy, or to filter or store data. In respect of cardiac monitoring, sensing and recording such additional physiologic signals as blood pressure, blood temperature, pH, blood gas type and blood gas concentration signals has been proposed.

One type of ideal physiologic sensor provides information concerning a patient's exercise level or workload and operates in closed loop fashion. In other words, such an ideal physiologic sensor operates to minimize divergence from an ideal operating point or set of points. Blood oxygen saturation provides a direct indication of the amount oxygen consumed by a patient when exercising. Moreover, in a rate responsive pacing context, oxygen saturation is generally inversely related to pacing rate. That is, as oxygen saturation decreases due to exercise, pacing rates correspondingly increase so that divergence from the optimum operating point is minimized. Thus, development of a reliable, accurate sensor for monitoring blood oxygen saturation for use in conjunction with an IMD is desirable.

Those skilled in the art have therefore toiled for years to develop an implantable oxygen sensor capable of not only accurately and reliably sensing blood oxygen saturation levels, but also of being manufactured easily at a reasonable cost. Such efforts have included attempts to develop systems for recording oxygen saturation and absolute pressure simultaneously, or to initiate or modify therapy on the basis of blood oxygen saturation. The exemplary prior art pertaining to implantable blood oxygen sensors includes the U.S. patents listed in Table 1 below.

Considerable effort has been expended in designing chronically implantable temperature sensors and relative or absolute pressure sensors. Nevertheless, a need still exists for a body implantable, durable, long-lived and low-power-consuming pressure sensor capable of accurately sensing absolute or relative pressure in the body over a period of many years. Likewise, a need still exists for a body implantable, durable, long-lived and low-power-consuming temperature sensor capable of accurately and reliably sensing temperature in the body over a period of many years.

Various medical devices have been developed to receive information from one or more physiologic sensors or transducers. A typical physiologic sensor transduces a measurable parameter of the human body, such as blood pressure, temperature or oxygen saturation for example, into a corresponding electrical signal. A conventional approach to attaching a physiologic sensor to a multiple conductor lead extending from an implantable medical device involves connecting the sensor to at least two conductors provided in the lead.

Connecting two physiologic sensors to an implantable medical device in a conventional manner typically involves connecting the medical device to two multiple conductor leads, with a dedicated lead connected to each of the two sensors. The additional number of leads and associated connection hardware generally complicates the design of the leads and medical device electronics, increases power consumption and the cost of the device, and reduces overall device reliability.

An improved approach to connecting a medical device to two or more physiologic sensors is disclosed in U.S. Pat. No. 5,593,430 issued to Renger. The disclosed approach involves connecting each of the sensors in parallel to a two conductor lead.

Various implementations of systems for sensing blood oxygen and pressure, or for interconnecting one or more physiologic sensors in an implantable medical device are known in the art. Some examples of such sensors may be found in the patents, patent applications or publications listed in Table 1 below. Note that we admit none of the patents, patent applications or publications set forth in Table 1 below as necessarily constituting prior art in respect of the present invention.

TABLE 1

| U.S. Pat./Document No. | Inventor(s) | Issue/Publication Date |
| --- | --- | --- |
| H1114 | Schweitzer et al. | December 1, 1992 |
| B1 4,467,807 | Bornzin | June 30, 1992 |
| 3,746,087 | Lavering et al. | July 17, 1973 |
| 3,847,483 | Shaw et al. | November 12, 1974 |
| 4,114,604 | Shaw et al. | September 19, 1978 |
| 4,202,339 | Wirtzfeld et al. | May 13, 1980 |
| 4,399,820 | Wirtzfeld et al. | August 23, 1983 |
| 4,407,296 | Anderson | October 4, 1983 |
| 4,421,386 | Podgorski | December 20, 1983 |
| 4,444,498 | Heinemann | April 24, 1984 |
| 4,467,807 | Bornzin | August 28, 1984 |
| 4,523,279 | Sperinde et al. | June 11, 1985 |
| 4,554,977 | Fussell | November 26, 1985 |
| 4,623,248 | Sperinde | November 18, 1986 |
| 4,651,741 | Passafaro | March 24, 1987 |
| 4,697,593 | Evans et al. | October 6, 1987 |
| 4,727,879 | Liess et al. | March 1, 1988 |
| 4,730,389 | Baudino et al. | March 15, 1988 |
| 4,730,622 | Cohen | March 15, 1988 |
| 4,750,495 | Moore et al. | June 14, 1988 |
| 4,791,935 | Baudino et al. | December 20, 1988 |
| 4,807,629 | Baudino et al. | February 28, 1989 |
| 4,807,632 | Liess et al. | February 28, 1989 |
| 4,813,421 | Baudino et al. | March 21, 1989 |
| 4,815,469 | Cohen et al. | March 28, 1989 |
| 4,827,933 | Koningetal. | May 9, 1989 |
| 4,830,488 | Heinze et al. | May 16, 1989 |
| 4,877,032 | Heinze et al. | October 31, 1989 |

TABLE 1-continued

| U.S. Pat./Document No. | Inventor(s) | Issue/Publication Date |
|---|---|---|
| 4,903,701 | Moore et al. | February 27, 1990 |
| 4,967,755 | Pohndorf | November 6, 1990 |
| 5,005,573 | Buchanan | April 9, 1991 |
| 5,040,538 | Mortazavi | August 20, 1991 |
| 5,052,388 | Sivula et al. | 1 October 1991 |
| 5,058,586 | Heinze | October 22, 1991 |
| 5,067,960 | Grandjean | November 26, 1991 |
| 5,113,862 | Mortazavi | May 19, 1992 |
| 5,176,138 | Thacker | January 5, 1993 |
| 5,199,428 | Obel et al. | 6 April 1993 |
| 5,267,564 | Barcel et al. | December 7, 1993 |
| 5,275,171 | Barcel | January 4, 1994 |
| 5,312,454 | Roline et al. | May 17, 1994 |
| 5,324,326 | Lubin | 28 June 1994 |
| 5,329,922 | Atlee, III | July 19, 1994 |
| 5,342,406 | Thompson | August 30, 1994 |
| 5,358,519 | Grandjean | October 25, 1994 |
| 5,377,524 | Wise et al. | 3 January 1995 |
| 5,411,532 | Mortazavi | May 2, 1995 |
| 5,438,987 | Thacker et al. | August 8, 1995 |
| 5,490,323 | Thacker et al. | February 13, 1996 |
| 5,535,752 | Halperin et al. | July 16, 1996 |
| 5,564,434 | Halperin et al. | October 15, 1996 |
|  | Prutchi et al. | 17 September 1996 |
| WO 80/01620 | Kraska et al. | August 7, 1980 |
|  | Renger | January 14, 1997 |
| 5,601,611 | Fayram et al. | February 11, 1997 |
| 5,743,267 | Nikolic et al. | April 28, 1998 |
| 5,758,652 | Nikolic et al. | June 2, 1998 |
| 5,788,647 | Eggers | August 4, 1998 |

All patents listed in Table 1 hereinabove are hereby incorporated by reference herein, each in its respective entirety. As those of ordinary skill in the art will appreciate readily upon reading the Summary of the Invention, the Detailed Description of the Various Embodiments, and the Claims set forth below, at least some of the devices and methods disclosed in the patents of listed herein may be modified advantageously in accordance with the teachings of the present invention.

SUMMARY OF THE INVENTION

The present invention has certain objects. That is, various embodiments of the present invention provide solutions to one or more problems existing in the prior art with respect to implantable physiologic sensors and interconnecting such sensors with implantable medical devices. Prior art sensors were incapable of providing absolute pressure data or of providing both pressure and oxygen data using one lead only. Prior art devices employing more than one sensor in a single lead also typically disposed the sensors in an end-to-end configuration, generally resulting in difficult assembly and connection of electrical components. Some prior art devices employed a transparent tube for housing oxygen sensors, leading to direct but spurious internal reflections of LED beams into adjoining detectors. Many prior art sensors were incapable of detecting tissue overgrowth on the lens thereof, or did not efficiently gather light reflected from a blood mass onto a light detector disposed within the sensor housing. Various embodiments of the present invention have the object of solving at least one of the foregoing problems.

In comparison to known implementations of implantable multiple sensor assemblies, various embodiments of the present invention may provide one or more of the following advantages: reducing the length, size and weight of a housing for a plurality of sensors, reducing the power required by a pair of physiologic sensors that derive power from an implantable medical device; increasing the reliability of an implantable medical device system which employs two or more sensors; interfacing different types of sensors incorporated in a multiple sensor assembly with a wide variety of implantable medical devices; simplifying lead construction; eliminating undesired backscatter or internal reflection or refraction of light beams into detectors; permitting absolute pressure to be measured simultaneous with the measurement of oxygen levels in the body; simplified and easy interconnection and assembly of components; more efficient gathering of light reflected from a blood mass onto a light detector; permitting oxygen sensor data to be ignored when the degree of tissue overgrowth on an oxygen sensor lens becomes excessive, and increasing the number of sensors that may be placed in an implantable sensor housing.

Some embodiments of the invention include one or more of the following features: a smaller diameter sensor assembly comprising a plurality of sensors; a shortened sensor assembly for a plurality of sensors; a lighter sensor assembly for a plurality of sensors; a lead containing two or more conductors connecting two or more physiologic sensor units connected electrically in series or parallel; a sensor assembly comprising two or more elongated housing members that are longitudinally-oriented, each housing member having mounted therein at least one sensor; a sensor assembly having disposed in one elongated housing member thereof at least one oxygen sensor, the oxygen sensor comprising a light emitter and a light detector; an oxygen sensor having a light emitter lens and a light detector lens spaced apart from one another; a light barrier disposed between a light emitter and a light detector for eliminating undesired internal backscatter, refraction or reflection of light to the light detector mounted within a sensor housing; a second self-test light detector mounted near the light emitter for detecting tisssue overgrowth; an anti-reflective or high index of refraction coating disposed on the inner surface of an oxygen sensor lens.

The foregoing Summary of the Invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 8 is a side view of one embodiment of a medical electrical lead having a sensor assembly of the present invention mounted thereon.

FIG. 9 shows an enlarged view of the sensor assembly portion of the medical electrical lead of FIG. 8.

FIG. 11 shows switching architecture for selectively activating and deactivating each of two sensors coupled to a pair of lead conductors in accordance with one embodiment of the present invention.

FIGS. 13(a) through 13(c) show side and end views of the sensor assembly shown in FIGS. 12(a) and 12(b).

FIG. 21 shows a perspective view of one embodiment of first and second elongated housing members of the present invention.

FIG. 22 shows a perspective view of the elongated housing members of FIG. 21 in a partially assembled state.

FIG. 25 shows a partially exploded view of an embodiment of the sensor assembly of the present invention having three elongated housing members.

FIG. 26 shows a partially exploded view of another embodiment of the sensor assembly of the present invention having four elongated housing members.

FIGS. 28(a) and 28(b) show two embodiments of an oxygen sensor lens coating of the present invention.

Figure 1:
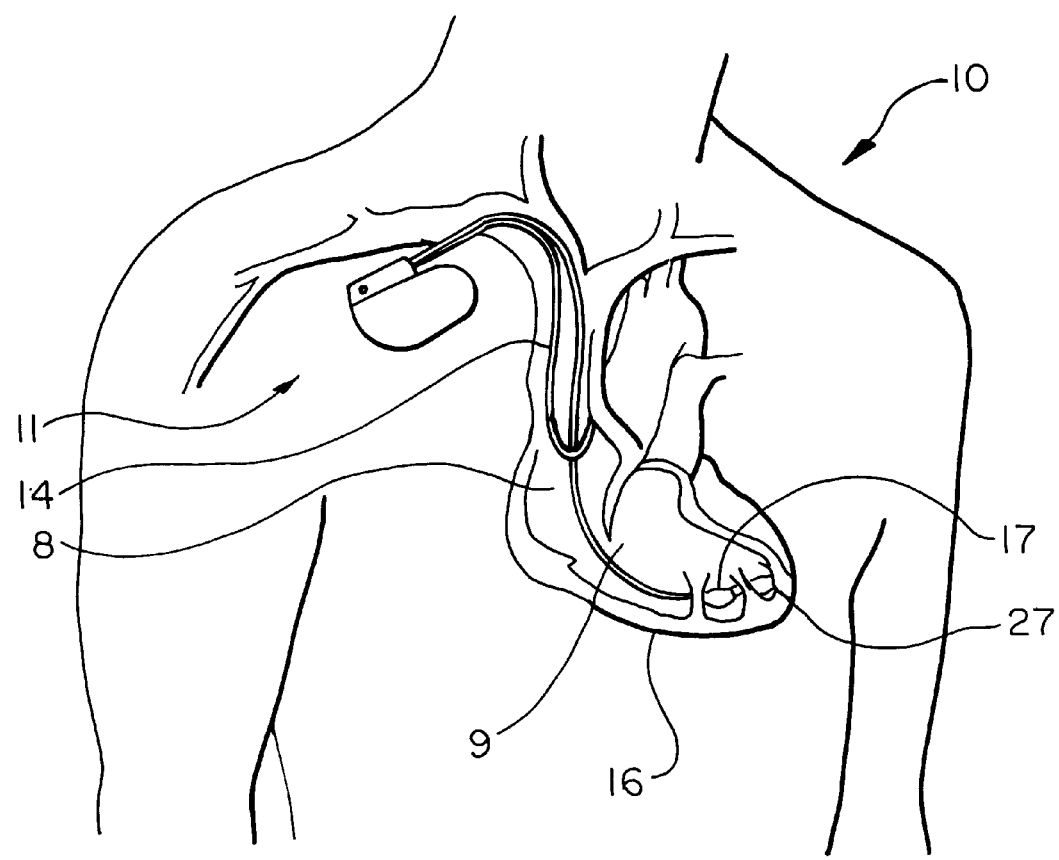
FIG. 1 shows an implantable medical device coupled to a sensor assembly in accordance with an embodiment of the present invention implanted in a human body.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the spirit and scope of the invention as defined by the appended claims.

DETAILED DESCRIPTION OF THE PREFERRED EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

U.S. patent application Ser. No. 09/177,540 filed Oct. 22, 1998 for "Circuit and Method for Implantable Dual Sensor Medical Electrical Lead" to Jonathan P. Roberts et al., hereby incorporated by reference herein, in its entirety, discloses circuits and methods for sensing physiologic signals with a two-conductor medical electrical lead that are preferred for use in connection with the invention described herein.

U.S. Pat. No. 5,902,326 to Lessar et al., hereby incorporated by reference herein, in its entirety, discloses optical windows and corresponding ferrules and other components for sensing blood oxygen saturation levels for a medical electrical lead that are preferred for use in connection with the invention described herein.

Referring now to FIG. 1, multiple sensor assembly 17 is attached to or forms part of lead 14 positioned in heart 16 of patient 10. Lead 14 is attached to implantable medical device (IMD) 11, shown implanted in the region of the upper right chest of patient 10.

Sensor assembly 17 may be implemented to operate in conjunction with a unipolar lead 14 or a bipolar lead 14 having, for example, two conductors 13 and 15, and may also be employed to operate in cooperation with a wide variety of implantable medical devices. In the case where IMD 11 is a pacemaker, one of two conductors 13 and 15 of lead 14 is typically connected between heart 16 and IMD 11. Lead 14, which typically includes a tined tip at its distal end 27 and at least tip electrode 5, senses electrical signals attendant to the depolarization and re-polarization of heart 16, and also transmits pacing pulses for causing depolarization of cardiac tissue in the vicinity of the electrode.

IMD 11 may be an implantable cardiac pacemaker, such as of the types disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties. IMD 11 may also be a pacemaker-cardioverter-defibrillator (PCD), one embodiment of which is further described below. The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. At least some of the devices disclosed in the foregoing patents may be employed in conjunction with sensor assembly 17 of the present invention.

Alternatively, IMD 11 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al. All the foregoing references are hereby incorporated herein by reference, each in its respective entirety.

In general, IMD 11 shown in FIG. 1 includes an hermetically-sealed enclosure that may include various elements, such as an electrochemical cell (e.g., a lithium battery), circuitry for controlling device operations and recording arrhythmic EGM episodes, a telemetry transceiver antenna and corresponding circuit for receiving downlinked telemetry commands from, and transmitting stored data by uplinked telemetry to, an external programmer.

Figure 2A:
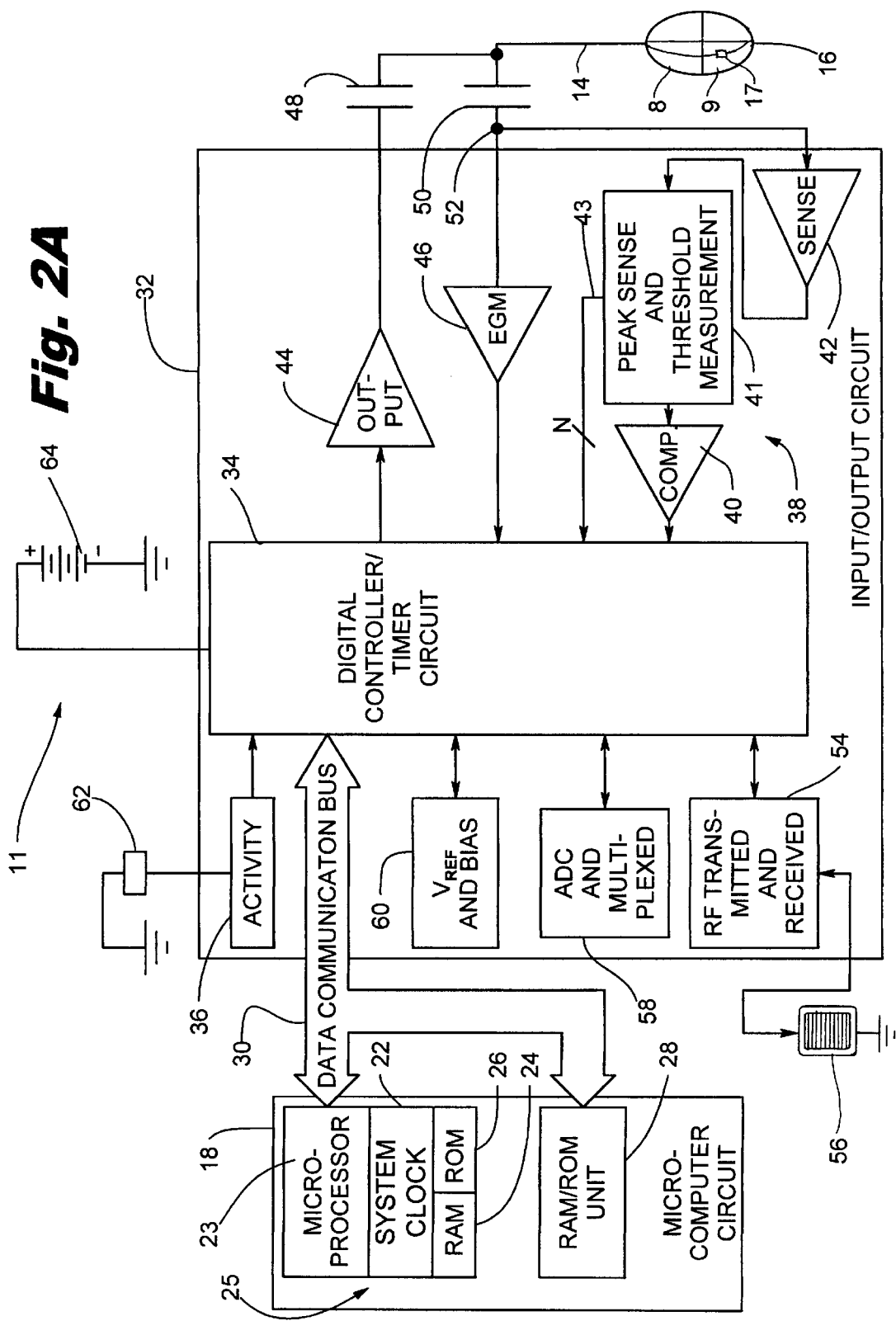
FIG. 2A shows an implantable pacemaker device coupled to a sensor assembly in accordance with one embodiment of the present invention.

FIG. 2A shows a block diagram illustrating various components of IMD 11 in the case where device 11 is a pacemaker. A pacemaker represents merely one of many implantable medical devices that may derive physiologic information from sensor assembly 17 of the present invention. In one embodiment of the present invention, pacemaker 11 is programmable by means of an external programming unit (not shown in the Figures). One such programmer suitable for the purposes of the present invention is the commercially available Medtronic Model 9790 programmer. This programmer is a microprocessor device which provides a series of encoded signals to pacemaker 11 by means of a programming head which transmits radio frequency (RF) encoded signals to pacemaker 11 according to a telemetry system such as that described in U.S. Pat. No. 5,312,453 to Wyborny et al., the disclosure of which is hereby incorporated by reference herein in its entirety. It is to be understood, however, that the programming methodology disclosed in the Wyborny et al. patent is identified herein for illustrative purposes only and that any programming methodology may be employed so long as the desired information is transmitted to and from pacemaker 11. One of skill in the art may choose from any of a number of available programming techniques to accomplish this task.

Pacemaker 11 in FIG. 2A is electrically coupled to patient's heart 16 by lead 14. Lead 14, which in one embodiment of the invention includes two conductors, is coupled to node 52 in the circuitry of pacemaker 11 through input capacitor 50. In one embodiment of the present invention, activity sensor 62 provides a sensor output to a processing/amplifying activity circuit 36 of input/output circuit 32. Input/output circuit 32 also contains circuits for interfacing with heart 16, antenna 56, and circuits 44 for application of stimulating pulses to heart 16 to moderate its rate under control of software-implemented algorithms in microcomputer unit 18.

Microcomputer unit 18 comprises on-board circuit 25 which includes microprocessor 20, system clock 22, and on-board RAM 24 and ROM 26. In this illustrative embodiment, off-board circuit 28 comprises a RAM/ROM unit. On-board circuit 25 and off-board circuit 28 are each coupled by a data communication bus 30 to digital controller/timer circuit 34. Electrical components shown in FIG. 2A are powered by an appropriate implantable battery power source 64 in accordance with common practice in the art. For purposes of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic disclosed in U.S. Pat. No. 4,566,063 issued to Thompson et al., hereby incorporated by reference herein in its entirety, or to that disclosed in the above-referenced Wyborny et al. patent. Voltage reference ($V_{REF}$) and bias circuit 60 generates a stable voltage reference and bias current for the analog circuits of input/output circuit 32. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of pacemaker 11 are coupled by data bus 30 to digital controller/timer circuit 34, where digital timers and counters establish the overall escape interval of the pacemaker as well as various refractory, blinking, and other timing windows for controlling the operation of the peripheral components disposed within input/output circuit 32. Digital controller/timer circuit 34 is preferably coupled to sensing circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41, in turn, provides an indication of peak sensed voltages and measured sense amplifier threshold voltages on path 43 to digital controller/timer circuit 34. An amplified sense amplifier signal is then provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 44 provides pacing stimuli to the patient's heart 16 through coupling capacitor 48 in response to a pacing trigger signal provided by digital controller/timer circuit 34. For example, each time the escape interval times out, an externally transmitted pacing command is received, or such commands are received in response to other stored commands as is well known in pacing art. Output amplifier 44, for example, may correspond generally to the output amplifier disclosed in U.S. Pat. No. 4,476,868 to Thompson, also incorporated by reference herein in its entirety.

Figure 2B:
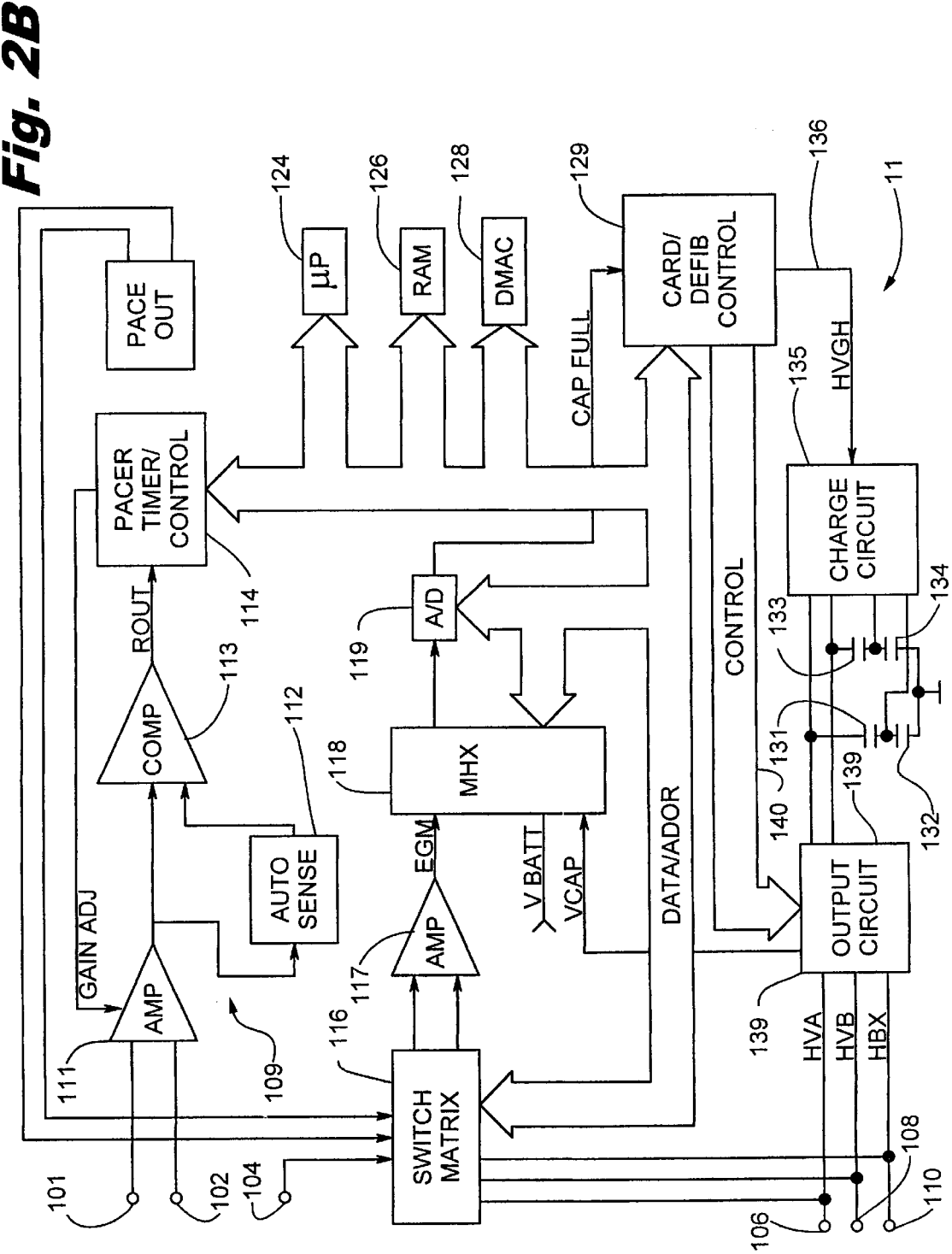
FIG. 2B shows one illustrative embodiment of a pacemaker/cardioverter/defibrillator unit coupled to a sensor assembly in accordance with another embodiment of the present invention.

FIG. 2B shows a functional schematic diagram adapted from U.S. Pat. No. 5,447,519 to Peterson. Implantable pacemaker-cardioverter-defibrillator (PCD) 11 represents another one of many implantable medical devices that may derive physiologic information from a sensor assembly of the present invention. U.S. Pat. No. 5,447,519 is incorporated by reference herein in its entirety. It is to be understood that this diagram is an illustration of an exemplary type of device in which the invention may find application, and is not intended to limit the scope of the present invention. Other implantable medical devices, such as those described previously, having functional organizations wherein the present invention may be useful, may also be modified to incorporate a sensor assembly in accordance with the present invention. For example, the present invention is also believed to be useful in conjunction with implantable PCDs such as those disclosed in U.S. Pat. No. 4,548,209 to Wielders, et al.; U.S. Pat. No. 4,693,253 to Adams et al.;

U.S. Pat. No. 4,830,006 to Haluska et al.; and U.S. Pat. No. 4,949,730 to Pless et al.; all of which are incorporated herein by reference, each in its respective entirety.

PCD 11 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 which includes band pass filtered amplifier 111, auto-threshold circuit 112, which provides an adjustable sensing threshold, and comparator 113. A signal is generated by the comparator 113 whenever the signal sensed between electrodes 101 and 102 exceeds the sensing threshold defined by auto-threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on data bus 115 to processor 124 and may act as an interrupt for processor 124 such that a particular routine of operations is commenced by processor 124.

Switch matrix 116 is used to select available electrodes under the control of processor 124 via data/address bus 115, such that the selection includes two electrodes employed as a far field electrode pair in conjunction with a tachycardia/fibrillation discrimination function. Far field EGM signals from the selected electrodes are passed through band pass amplifier 117 and into multiplexer 118, where they are converted to multi-bit digital data signals by A/D converter 119 for storage in random access memory 126 under the control of direct memory address circuitry 128.

Processor 124 may perform various morphology detection functions. For example, such detection functions may be indicative of tachycardia or fibrillation, or various other functions may be performed as set out in numerous references including any of the references incorporated herein by reference and others with regard to implantable PCDs.

The remainder of device 11 of FIG. 2B is dedicated to the provision of cardiac pacing, cardioversion, and defibrillation therapies. The pacer timing/control circuit 114 includes programmable digital counters that control the basic timing intervals associated with cardiac pacing. Further, under control of processor 124, pacer timing/control circuit 114 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 124 into pacer timing and control circuitry 114. Similarly, in the event that generation of a cardioversion or defibrillation pulse is required, processor 124 employs the timing and control circuitry 114 to control timing of such cardioversion and defibrillation pulses.

In response to detection of fibrillation or tachycardia requiring a cardioversion pulse, processor 124 activates cardioversion/defibrillation control circuitry 129, which initiates charging of the high voltage capacitors 131–134 via charging circuit 135 under the control of high voltage charging line 136. Thereafter, delivery and timing of the defibrillation or cardioversion pulse is controlled by pacer timing/control circuitry 114. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety.

Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all of which are incorporated herein by reference in their respective entireties. Moreover, known circuitry for controlling the timing and generation of anti-tachycardia pacing pulses is described in U.S. Pat. No. 4,577,633 to Berkovits et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

Selection of a particular electrode configuration for delivery of the cardioversion or defibrillation pulses is controlled via output circuit 139 under the control of cardioversion/defibrillation control circuit 129 via control bus 140. Output circuit 139 determines which of the high voltage electrodes 106,108 and 110 is to be employed in delivering the defibrillation or cardioversion pulse regimen.

Figure 3:
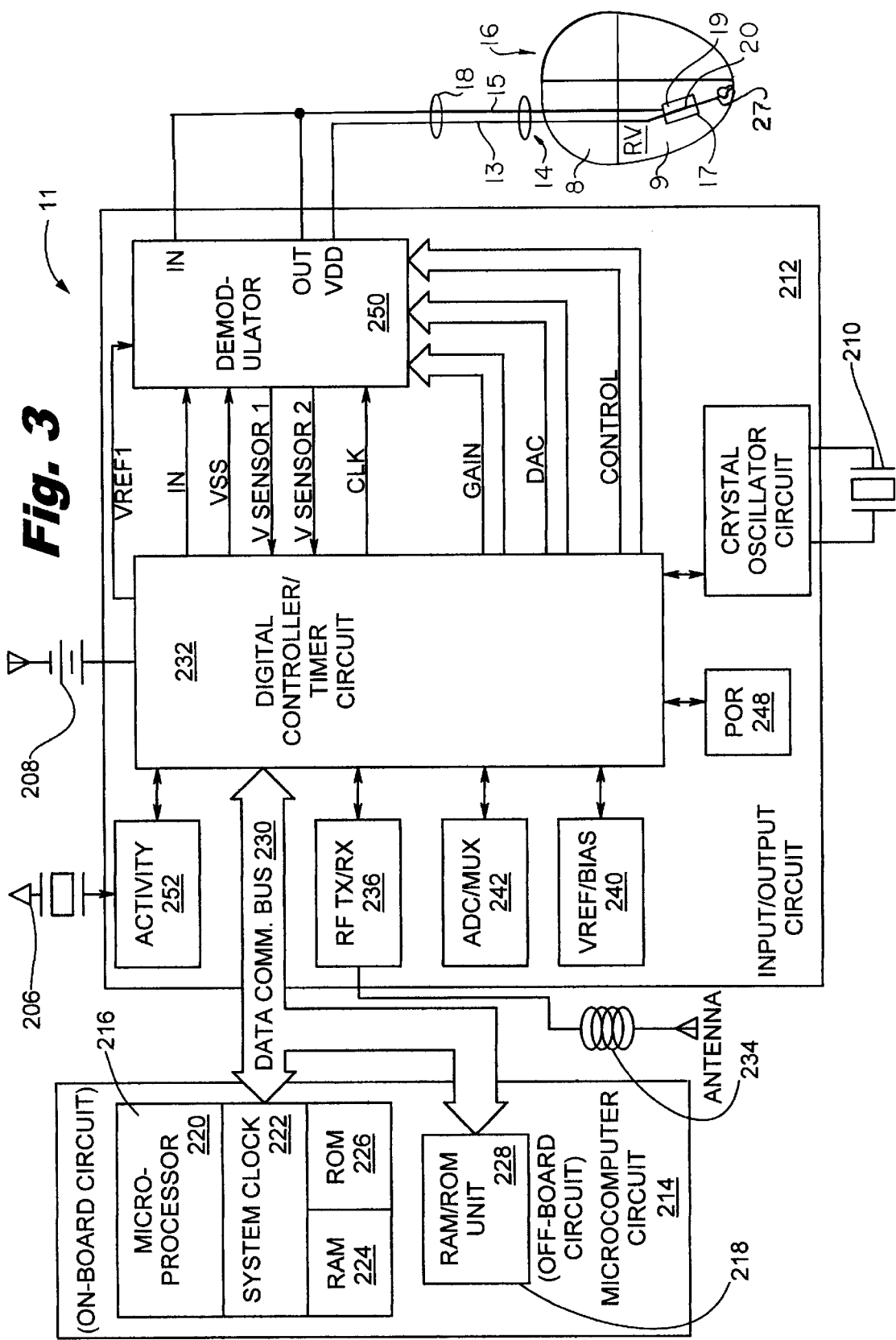
FIG. 3 shows an implantable medical device including a sensor assembly in accordance with a further embodiment of the present invention.

FIG. 3 shows a block diagram of an implantable programmable monitor and corresponding lead system which represents yet another implantable medical device that may derive physiologic information from multiple sensor assembly 17 of the present invention. Implantable monitor 11 may be configured as a standalone system, or alternatively may be configured as part of pacemaker, IPG, PCD, ICD, nerve stimulator or other implantable medical device.

FIG. 3 illustrates patient's heart 16 in relation to lead 14 and sensor assembly 17 in accordance with one embodiment of the present invention. Lead 14 includes first and second lead conductors 13 and 15 extending from or near sensor assembly 17 disposed near distal end 27. Distal end 27 most preferably includes soft pliant tines adapted to catch trabeculae carnae disposed in the ventricles of heart tissue to stabilize lead 14 in a manner well known in the art.

Monitor 11 generally comprises input/output circuit 212 coupled to battery 208, optional activity sensor 206, telemetry antenna 234, lead conductors 13 and 15, crystal 210, and microcomputer circuit 214. Input/output circuit 212 includes digital controller/timer circuit 232 and associated components, including crystal oscillator 238, power-on-reset (POR) circuit 248, $V_{ref}$/BIAS circuit 240, ADC/MUX circuit 242, RF transmitter/receiver circuit 236, optional activity circuit 252, and sensor signal demodulator 250.

Crystal oscillator circuit 238 and crystal 210 provide the basic timing clock signals for the digital controller/timer circuit 232. Voltage Reference ($V_{ref}$)/BIAS circuit 240 generates stable voltage reference $V_{ref}$ and current levels from battery 208 for the circuits within the digital controller/timer circuit 232, and the other identified circuits including microcomputer circuit 214 and demodulator 250. Power-on-reset circuit 248 responds to initial connection of the circuitry to battery 208 for defining an initial operating condition and also resets the operating condition in response to detection of a low battery voltage condition. Analog-to-digital converter (ADC) and multiplexer circuit 242 digitizes analog sensor signals received by digital controller/timer circuit 232 from demodulator 250 for storage by microcomputer circuit 214.

Data signals transmitted out through RF transmitter/receiver circuit 236 during telemetry are multiplexed by ADC/MUX circuit 242. Voltage reference and bias circuit 240, ADC/MUX circuit 242, POR circuit 248, crystal oscillator circuit 238, and optional activity circuit 252 may correspond to any of those previously described herein or presently used in current marketed, implantable cardiac pacemakers.

Digital controller/timer circuit 232 includes a set of timers and associated logic circuits connected with microcomputer circuit 214 through the data communications bus 230. Microcomputer circuit 214 contains on-board chip including microprocessor 220, associated system clock 222, and on-board RAM and ROM chips 224 and 226, respectively. In addition, microcomputer circuit 214 includes off-board circuit 218 including separate RAM/ROM chip 228 to provide additional memory capacity. Microprocessor 220 is interrupt driven, operating in a reduced power consumption mode normally, and awakened in response to defined interrupt events, which may include the periodic timing out of data sampling intervals for storage of monitored data, the transfer of triggering and data signals on bus 230, and the receipt of programming signals. A real time clock and calendar function may also be included to correlate stored data to time and date.

In a further variation of the present invention, provision may be made for the patient to initiate storage of the monitored data through an external programmer or a reed switch closure when an unusual event or symptom is experienced. The monitored data may be related to an event marker on later telemetry out and examination by the physician.

Microcomputer circuit 214 controls the operating functions of digital controller/timer 232, specifying which timing intervals are employed, and controlling the duration of the various timing intervals, via bus 230. The specific current operating modes and interval values are programmable. The programmed-in parameter values and operating modes are received through antenna 234, demodulated in RF transmitter/receiver circuit 236, and stored in RAM 224.

Data transmission to and from the external programmer (not shown) is accomplished by means of telemetry antenna 234 and the associated RF transmitter and receiver 236, which serves both to demodulate received downlink telemetry and to transmit uplink telemetry. For example, circuitry for demodulating and decoding downlink telemetry may correspond to that disclosed in previously referenced U.S. Pat. No. 4,556,063 and U.S. Pat. No. 4,257,423 issued to McDonald et al., while uplink telemetry functions may be provided according to U.S. Pat. No. 5,127,404 issued to Wyborny et al., all which are hereby incorporated by reference herein in their respective entireties. Uplink telemetry capabilities typically include the ability to transmit stored digital information as well as real time physiologic sensor signals, such as blood pressure signals, for example.

A number of power, timing, and control signals are applied by the digital controller/timer circuit 232 to demodulator 250 to selectively initiate and power the operation of each of the at least two independent physiologic sensors 19 and 20 included within sensor assembly 17, and to selectively read out the applicable signals generated by first and second sensors 19 and 20, respectively. Monitor 11 periodically stores digitized data related to the various physiologic parameters sensed by the sensor assembly 17 at a nominal sampling frequency which may be related to patient activity level, both optionally correlated to time and date and patient initiated event markers. Depending on the particular configuration of sensor assembly 17, pertinent physiologic parameters, such as parameters relating to patient activity, blood pressure or temperature, blood oxygen or other gas saturation level, and electrogram (EGM) status, may be continuously monitored.

Figure 4:
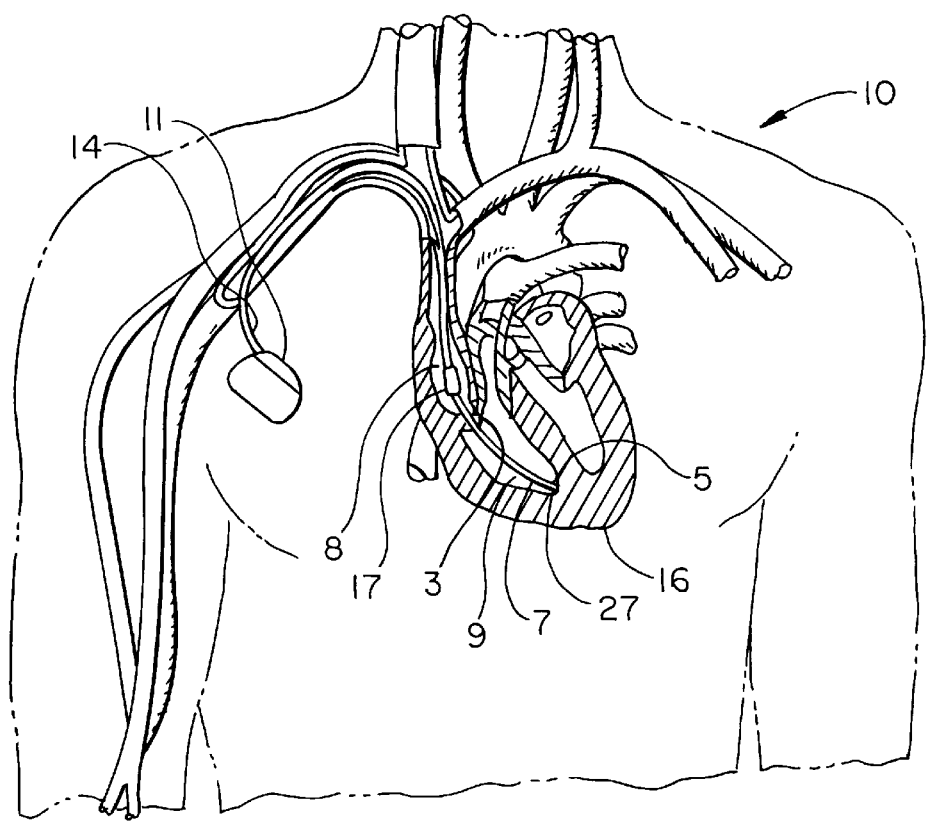
FIG. 4 illustrates an implantable medical device implanted in a human being and having a medical electrical lead attached thereto.

FIG. 4 illustrates IMD 11 implanted in patient 10 and having medical electrical lead 14 attached thereto, and also illustrates typical positioning and placement of IMD 11 and lead 14 within the right upper chest of patient 10. Lead 14 is generally introduced transvenously into heart 16 through tricuspid valve 3 to locate distal tip 27, tip electrode 5 and ring electrode 7 in right ventricular chamber 9. Oxygen sensor 20 of sensor assembly 17 is typically positioned in right atrial chamber 8 or right ventricular chamber 9.

In a hemodynamic monitoring context, IMD 11 typically records EGMs sensed between electrodes 7 and 5 and the output signal provided by oxygen sensor 20 of multiple sensor assembly 17. IMD 11 may record oxygen saturation data continuously, periodically at predetermined intervals, or only when a triggering event is sensed.

In a rate responsive pacing context, IMD 11 is a ventricular pacing pulse generator that operates in a rate responsive, demand pacing mode. IMD 11 may establish a pacing escape interval determined by a rate response algorithm. Such an algorithm typically computes escape intervals on the basis of sensed venous blood oxygen levels, and directs delivery of pacing pulses to electrodes 5 and 7, unless R-waves are sensed within the escape interval. A monitoring function may also be incorporated into IMD 11.

In a rate responsive pacing context, oxygen sensor 20 is most preferably positioned within an area of a living body where flowing venous blood contacts light energy emitted by one or more light emitting diodes (light emitters) disposed within or forming part of oxygen sensor 20. Oxygen sensor 20 may be placed either within a vein that is carrying blood back to heart 16, within right atrium 8 or within right ventricle 9. It is generally preferred that oxygen sensor 20 be positioned on lead 14 and sensor assembly 17 such that oxygen sensor 20 is located propinquant to ring electrode 7 within right atrium 8 of heart 16. It is generally believed that sensing the oxygen saturation of blood located within right atrium 8 may provide a most sensitive indication of patient exercise levels. Other locations for sensing oxygen saturation of venous blood include the right ventricle (more about which we say below) and the pulmonary artery. Yet other locations for sensing oxygen saturation of arterial blood include the left ventricle and left atrium, as well as the aorta or peripheral arterial vasculature.

When positioned properly within heart 16, lead 14 may be curved or configured such that light emitting and detecting elements of oxygen sensor 20 face blood 167 just before it passes through tricuspid valve 3. For a complete discussion of the manner in which an oxygen sensor may be optimally positioned in right atrium 8 as a control mechanism for a rate responsive pacemaker, see U.S. Pat. No. 5,076,271, hereby incorporated by reference herein in its entirety.

In FIG. 4, oxygen sensor 20 forms a module incorporated into sensor assembly 17, which in turn is incorporated into lead 14 at a location intermediate between the proximal and distal ends of lead 14. Oxygen sensor 20 is typically mechanically and electrically coupled to the distal ends of lead conductors disposed within the body of lead 14. Connector elements disposed at the proximal ends of lead 14 are connected to appropriate terminals in IMD 11.

Figure 5:
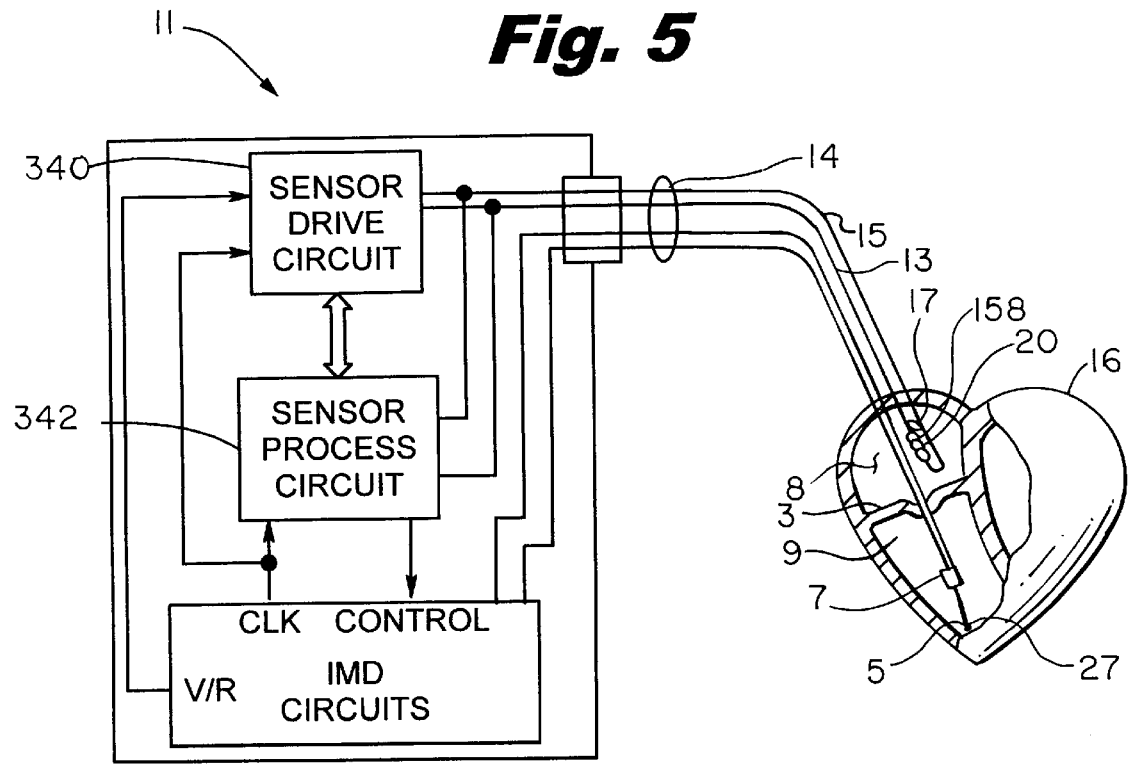
FIG. 5 shows a block diagram of an implantable medical device system comprising an IMD and a medical electrical lead having an oxygen sensor attached thereto.

FIG. 5 shows a block diagram of an implantable medical device system comprising IMD 11 and medical electrical lead 14 having second physiologic sensor 20 (in this case an oxygen sensor) attached thereto. Input and output terminals of oxygen sensor 20 are coupled through lead conductors 13 and 15 of lead 14 to sensor drive circuit 340 and sensor processor circuit 342. Examples of the manner in which oxygen sensor drive circuit 340 and processor circuit 342 operate are described in the above-incorporated '987 and '389 patents.

Figure 6:
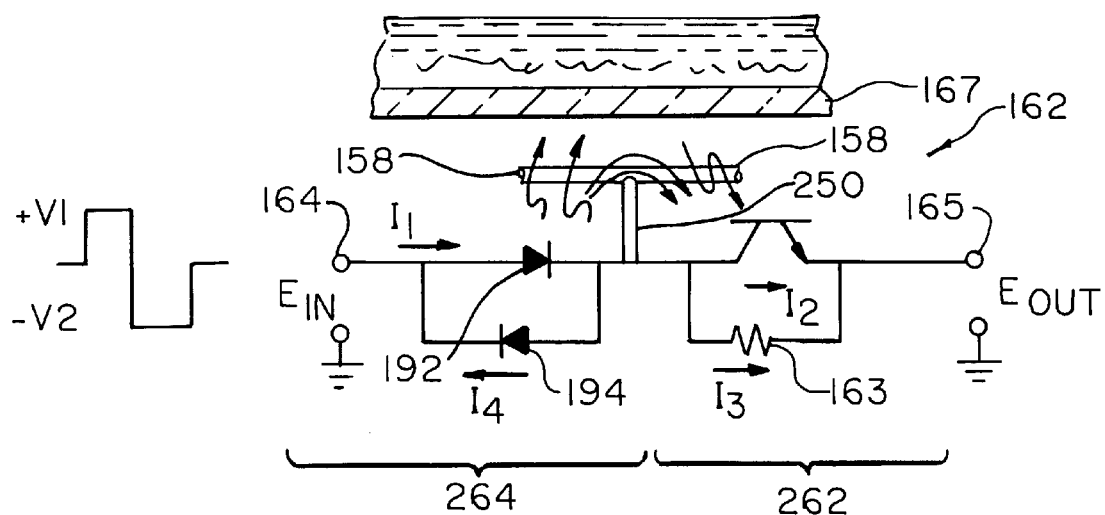
FIG. 6 shows a circuit diagram of prior art oxygen sensor circuitry and corresponding sensor optical structure.
Figure 7:
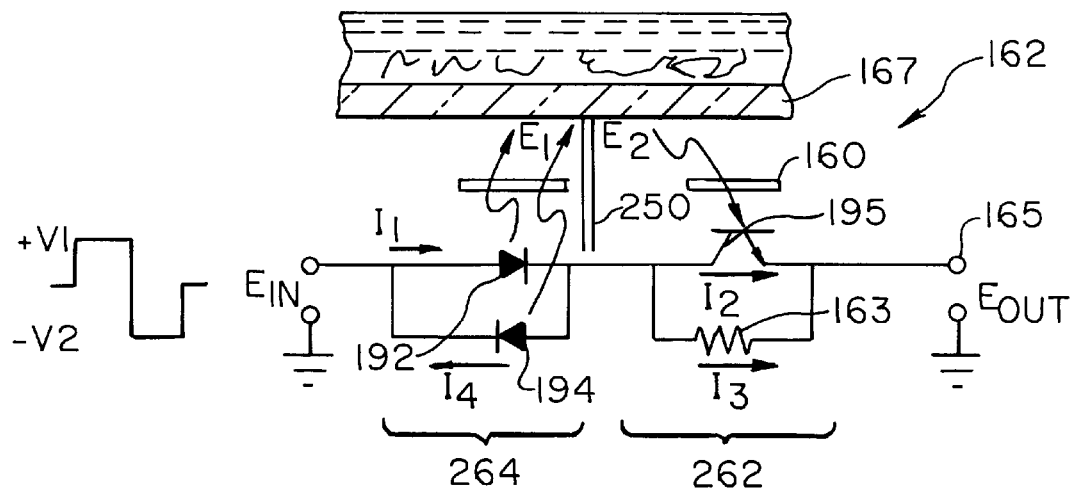
FIG. 7 shows a circuit diagram of oxygen sensor circuitry and corresponding optical structure of the present invention.

FIG. 6 shows a circuit diagram of prior art oxygen sensor circuitry and corresponding prior art oxygen sensor optical structure. FIG. 7 shows a circuit diagram of oxygen sensor circuitry and corresponding oxygen sensor optical structure of the present invention.

FIG. 6 illustrates one difficulty in employing a conventional prior art light barrier 280 disposed between light emitting portion 264 and light detecting portion 262 of oxygen sensor 20. In FIG. 6, prior art light barrier 280 extends only to the interior surface of single transparent cover or lens 158, and not through cover or lens 158 to the exterior surface thereof. As a result, light emitted by light emitters 192 and 194 may refract through lens 158, or internally reflect from the boundary disposed between the body of lens 158 and its outer surface, to emerge into light detecting portion 262 of oxygen sensor 20 for detection by light detector or photosensor 195. Consequently, and as the inventors of the present invention have discovered, light emitted by light emitters 192 and 194 that is not reflected by blood mass 167, and therefore is completely unrelated to blood oxygen saturation levels, may be detected by detector 195 and sensed along with light beams reflected from blood mass 167. Detector 195 is incapable of separating light beams impinging upon it on the basis of their reflective or refractive origin, and thus generates an estimate of blood oxygen saturation that is in error by an amount that corresponds at least to the relative proportion of light not reflected by blood mass 167 impinging upon detector 195.

Figure 10:
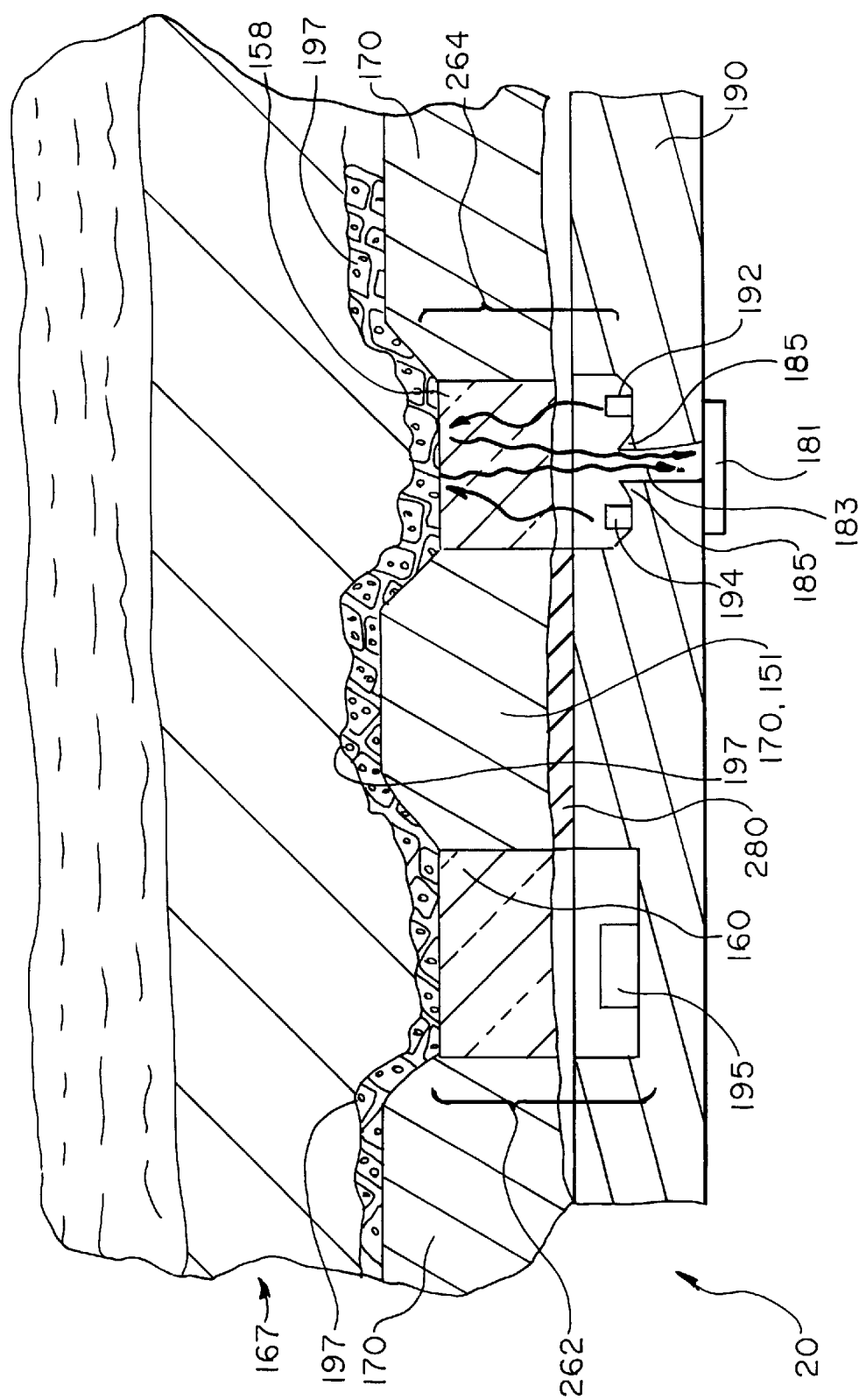
FIG. 10 shows a cross-sectional view of one embodiment of an oxygen sensor of the present invention.
Figure 13D:
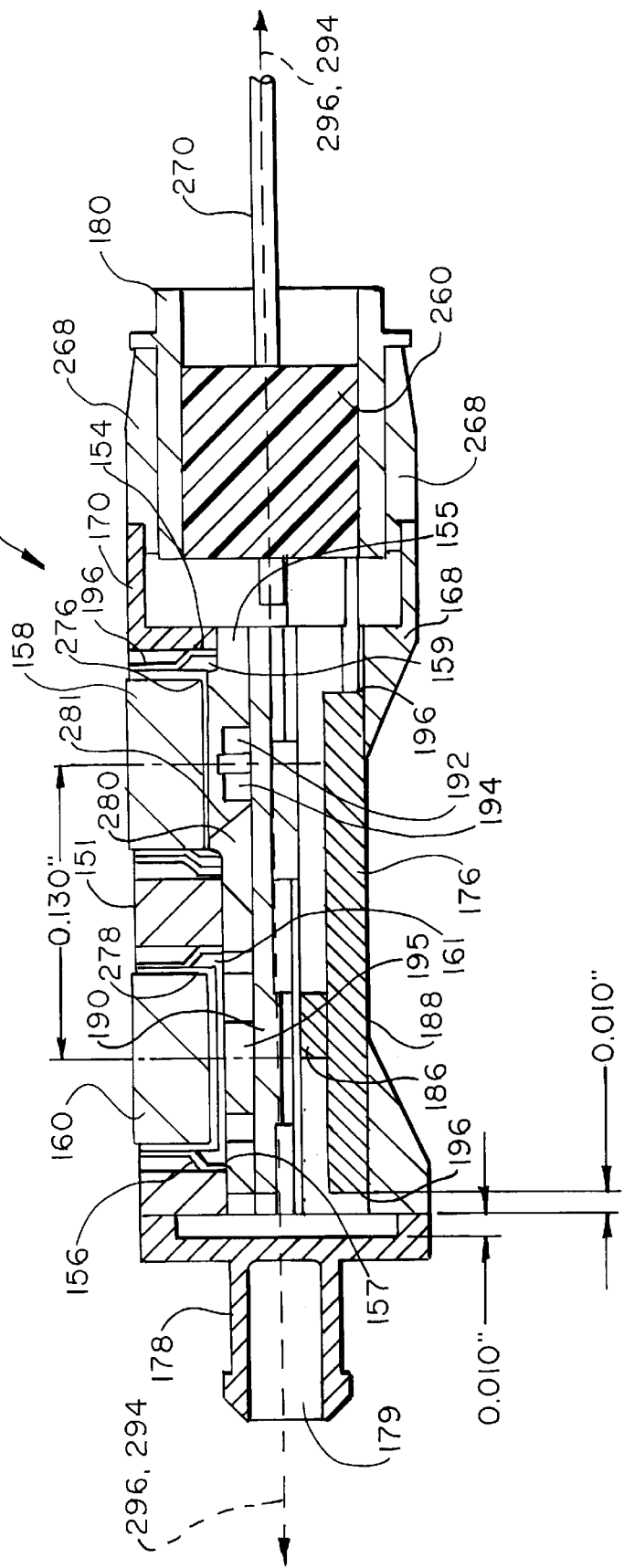
FIG. 13(d) shows a cross-sectional view of the sensor assembly shown in FIGS. 12(a) through 13(c).
Figure 14:
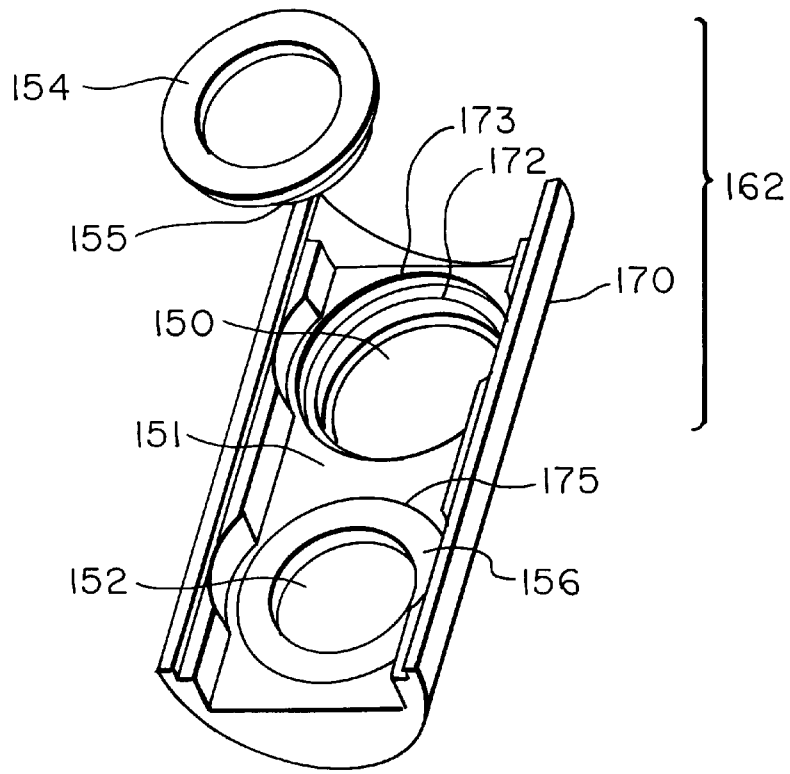
FIG. 14 shows one embodiment of a portion of an elongated housing member of the present invention.
Figure 15:
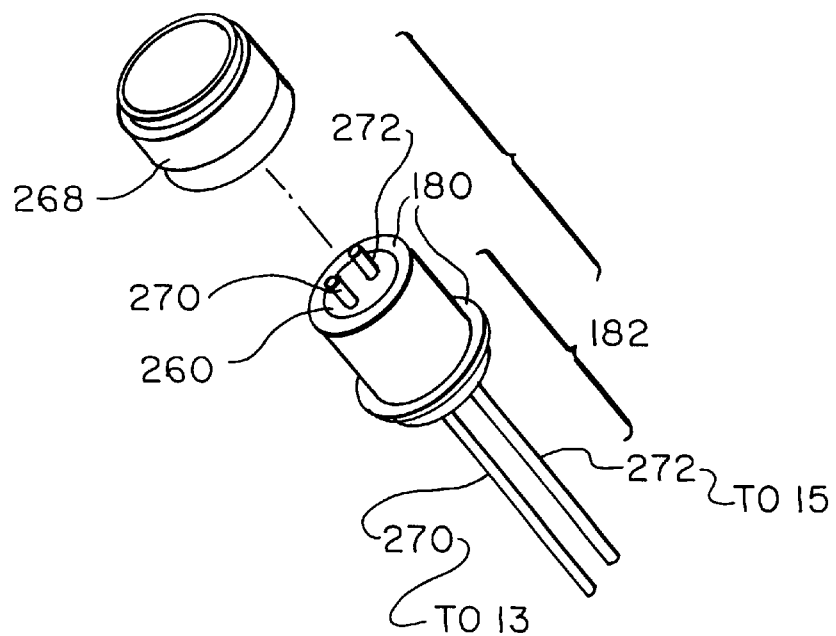
FIG. 15 shows an adapter sleeve and corresponding feedthrough assembly of one embodiment of the present invention.

Referring now to oxygen sensor 20 of the present invention shown in FIG. 7, oxygen sensor 20 includes light barrier or baffle 280 disposed between light emitting portion 264 and light detecting portion 262. Light detecting portion 264 most preferably has its own discrete lens 158 separated from lens 160 of light detecting portion 262. Light barrier 280 prevents the direct, reflected or refracted transmission of light that is not reflected by blood mass 167 into light detecting portion 262 for spurious detection by detector 195. As shown in FIGS. 10 and 13(d), light barrier 280 may comprise additional elements which serve light barrier functions such as elongated housing member light barrier 151 and/or at least portions of second elongated housing member 170. Lenses 158 and 160 are typically formed of either a flat panel, cylinder or half-cylinder of glass, sapphire, ruby, quartz or any other suitable light transmissive material.

Continuing to refer to FIG. 7, first light emitter or LED 192 and optional second light emitter or LED 194 are most preferably disposed or mounted within second elongated housing member 170 of sensor assembly 17. First and second light emitters 192 and 194 most preferably sequentially emit light having a first blood oximetry frequency and a second blood oximetry frequency, respectively. It is preferred that the second blood oximetry frequency be in the infrared portion of the light spectrum. Light emitters 192 and 194 are most preferably mounted on an upper surface of oxygen sensor hybrid 190 (not shown in FIG. 7, but shown in FIGS. 10, 13(d) and 18 through 21) at light emitter locations separated from a light detector location.

Photosensor or light detector 195 most preferably sequentially senses the intensity of light originating from light emitters 192 and 194 that is reflected from blood cells in adjoining blood mass 167. Photosensor or light detector 195 is most preferably mounted on an upper surface of oxygen sensor hybrid 190 (not shown in FIG. 7, but shown in FIGS. 10, 13(d) and 18 through 21) at a light detector location separated from the light emitter locations.

Oxygen sensor circuit 162 shown in FIG. 7 includes resistor 163 coupled to light emitters 192 and 194 and to photosensor 195, and further includes input and output terminals 164 and 165. In one embodiment of the present invention, input and output terminals 164 and 165 are coupled through lead conductors 13 and 15 of lead 14 to sensor drive circuit 340 and sensor processor circuit 342 of FIG. 5.

FIG. 8 is a side view of one embodiment of a medical electrical lead having sensor assembly 17 of the present invention mounted thereon. FIG. 9 shows an enlarged view of sensor assembly 17 of the medical electrical lead of FIG. 8, where in accordance with one embodiment of the present invention multiple sensor assembly 17 comprises first elongated housing member 168 housing a first sensor 19 (such as a pressure sensor, for example) and second elongated housing member 170 housing a second sensor 20 (such as an oxygen sensor, for example), and further has separate wells or sensor portions, and corresponding discrete lenses 158 and 159, for receiving light emitters 192 and 194, and light detector 195, therein.

FIG. 10 shows a cross-sectional view of one embodiment of oxygen sensor 20 of the present invention. A light barrier is formed by the combination of light barrier 280 and elongated housing member light barrier 151 (which most preferably is integral to and forms a portion of second elongated housing member 170).

FIG. 10 illustrates a common problem concerning sensors chronically implanted within the human body. Namely, at least portions of an implantable medical device often develop over time tissue or fibers 197 that grow over or extend onto exterior portions of the device. FIG. 10 illustrates a particularly acute case where tissue or fibers 197 have encased the exterior portions of second elongated housing member 170 of chronically implanted sensor assembly 17 to such an extent that lenses 158 and 160 of oxygen sensor 20 are covered or partially covered with tissue or fibers 197.

As will now become apparent, tissue or fibers 197 obscuring at least portions of lens 158 reduce the amount of light originating from light emitters 192 and 194 that may pass through lens 158 for reflection from blood mass 167. Likewise, tissue or fibers 197 obscuring at least portions of lens 160 reduce the amount of light reflecting off blood mass 167 for detection by light detector 195.

The blockage or obstruction of lenses 158 and 160 by tissue or fibers 197 may lead to errors in calculating or measuring oxygen concentration levels in blood mass 167. When detector 195 receives or detects little light impinging thereon it is incapable of distinguishing between a first circumstance where the blood oxygen concentration of blood mass 167 is very low (and thus the amount of light originating from light emitters 192 and 194 and reflecting off blood mass 167 is very low), and a second circumstance where the blood oxygen concentration of blood mass 167 is relatively high, but tissue or fibers 197 obscure lenses 158 or 160.

Self-test light detector 181 shown in FIG. 10 helps overcome the foregoing problem by providing an estimate of the amount of light emitted by light emitters 192 and 194 that is reflected back into light emitter portion 264 (instead of being transmitted through lens 158 for reflection from blood mass 167). Self-test light detector 181 may be a photosensor or photodiode of a type well known in the art.

An output signal from self-test light detector 181 may be employed to calibrate or adjust the output signal provided by light detector 195 in such a manner that the estimate of blood oxygen saturation levels otherwise provided by or proportional to the output signal from light detector 195 is compensated or adjusted to account for the degree or amount of tissue overgrowth of lenses 158 and 160 of oxygen sensor 20. Alternatively, once an output signal of a predetermined threshold or amplitude is provided by self-test light detector 181 to means for detecting the predetermined light threshold, such means can further be employed to cause oxygen saturation data generated in response to signals provided by light detector 195 to be ignored or assigned less weight or reliability by circuit or microprocessor means disposed in implantable medical device 11, integrated circuit 191, or otherwise disposed in oxygen sensor 20.

The operation of self-test light detector 181 may be improved by providing a light gathering device on or near light detector channel 183 such that light rays originating at light emitters 192 and 194 and reflected back towards self-test light detector 181 by tissue overgrowth disposed over at least portions of lens 158 are gathered by, for example, a reflector or series of closely spaced reflective surfaces which guide light so reflected towards self-test light detector. Light detector 181 may further comprise a plurality of light detectors, or may be integrated into or mounted upon oxygen sensor hybrid 190. Like light detector 198, light detector 181 may sequentially sense light.

At least some light rays reflected from the underside of tissue or fibers 197 overgrowing lens 158 are directed into self-test light detector channel 183 for detection by light detector 181. The upper portions of self-test light detector channel 183 most preferably include upwardly extending rims, reflective surfaces 185 that prevent direct light rays emitted by light emitters 192 and 194 from entering light detector channel 183 for undesired detection by self-test light detector 181. Rims or reflective surfaces 185 may also be configured or shaped to outwardly collimate or direct light beams towards lens 158 that emanates from light emitters 192 and 194.

Signal outputs originating from self-test light detector 181 may be directly combined or mixed with, or subtracted from, the signal outputs provided by light detector 195 to thereby correct or adjust the estimate of blood oxygen saturation provided by light detector 195. Alternatively, the two outputs provided by detectors 181 and 195 may be multiplexed up conductors 13 and 15 in a fashion similar to that shown in FIG. 11, or may otherwise be conveyed to IMD 11 for separate amplification and processing in microprocessor 23/216. Other means of processing the output signals provided by light detectors 181 and 195 to provide an estimate of the amount by which light sensed at detector 195 should be adjusted to compensate for tissue overgrowth are contemplated in the present invention as well. Those alternative means include providing digital signal processing (DSP) or microprocessor means within sensor assembly 17 to process output signals provided by light detectors 181 and 195.

In the present invention, it may be preferred that conductors coupled to first and second sensors 19 and 20 of sensor assembly 17 function independently from, or at times different than, conductors employed for stimulating tip or ring electrodes 5 and 7 so that interference with basic operation of IMD 11 is prevented.

Referring now to FIG. 11, there is shown one embodiment of sensor assembly 17 which includes two sensors 19 and 20, each of which senses one or more physiologic parameters associated with the human heart 16. Lead 14 includes two conductors 13 and 15. Each of two sensors 19 and 20 included within sensor assembly 17 is coupled to one or both of the two conductors 13 and 15 in either a series or parallel configuration.

Two sensors 19 and 20 of sensor assembly 17 are selectively and alternately activated and deactivated in a manner appropriate for a particular physiologic sensor and monitoring application. In one embodiment, power is selectively applied to one of two sensors 19 and 20 of sensor assembly 17 and concurrently removed from the other one of the two sensors 19 and 20, which advantageously reduces power consumption.

Controlling the application and removal of power to and from selected sensors 19 and 20 of sensor assembly 17 in this manner may significantly reduce the overall power requirements of medical device 21 and extend battery life. A conventional power control approach, in contrast, is generally incapable of applying and removing power to selected sensors coupled to a two conductor lead. Rather, such prior art schemes typically require that power be applied to all sensors concurrently and removed from all sensors concurrently, even when only one of the sensors need be active or inactive during a given period of time.

Signals produced by each of sensors 19 and 20 are transmitted to IMD 11 during the time in which a selected sensor is operational. As such, each sensor 19 and 20 is afforded exclusive use of the lead conductors 13 and 15 to effect communications with IMD 11. This manner of controlling sensor assembly 17 obviates the need for employing complex addressing and time or frequency modulation/demodulation techniques associated with prior art schemes that require usage of a common pair of lead conductors. The simple yet elegant methodology for controlling a sensor assembly 17 in accordance with the principles of the present invention provides for increased reliability and reduced power consumption, two advantages which are of particular importance in the medical device industry.

In one embodiment of the present invention, sensors 19 and 20 of sensor assembly 17 are selectively activated and deactivated for operation in response to variations in the polarity of a supply voltage generated by IMD 11 and applied to conductors 13 and 15. One of two sensors 19 and 20 of sensor assembly 17 may be operated for a period of time similar to or different from the other sensor 19 or 20.

By way of example, and assuming that a pressure sensor and an oxygen saturation sensor constitutes sensor 20 of sensor assembly 17, pressure sensor 19 may be operated for a period of time during each depolarization/re-polarization cycle of heart 16. Oxygen saturation sensor 20, in contrast, may be operated for a period of time during every third depolarization/re-polarization cycle of heart 16.

It can be readily appreciated from this illustrative example that powering oxygen sensor 20 only when required (e.g., once every third depolarization/re-polarization cycle) can reduce the power requirement for oxygen sensor 20 by as much as 66 percent in comparison to a scheme which requires concurrent delivery of power to pressure and oxygen sensors 19 and 20. A sensor assembly and control methodology implemented in accordance with the principles of the present invention advantageously provides an elegant, low power, and reliable approach to selectively monitoring two or more physiologic parameters associated with human heart 16 or other organ using only two conductors 13 and 15 of lead 14.

FIG. 11 further shows a block diagram useful for describing one embodiment of a circuit and method of a sensor assembly 17 and IMD 11 according to the present invention. In accordance with this illustrative embodiment, sensor assembly 17 includes two sensors, sensor 19 and sensor 20, each of which senses one or more physiologic parameters associated with a human heart or other organ. Sensors 19 and 20 represent two sensors which may be fabricated as discrete, or alternatively as, integral IC components. Switch 306 is coupled to sensors 19 and 20 and to one conductor 13 of two conductor lead 14. Sensors 19 and 20 are also coupled to second conductor 15 of lead 12. The construction and configuration of conductors 13 and 15, and the attachments made thereto, may be of a conventional type as is well known in the art.

Conductors 13 and 15 are coupled to control unit 304. Control unit 304 is intended to represent a component or set of components that perform the general functions of controlling the state of two conductors 13 and 15 and coordinating the transmission and reception of signals thereover. Control unit 304, for example, may represent a controller circuit, such as digital controller/timer circuit 232 shown in FIG. 3, or a control circuit incorporating the functionality of a decoder circuit, such as demodulator 250, also shown in FIG. 3. Control unit 304 may further be representative of a microprocessor, such as microcomputer circuit 214 shown in FIG. 3, alone or in combination with other components shown in FIG. 3. Various signals transmitted between sensors 19 and 20, and control unit 304 may be processed or produced by other components via signal conductors 23 and 25.

As is further shown in FIG. 11, tip electrode 5, typically incorporating a tined tip structure, is usually connected to appropriate heart or other organ tissue as discussed previously. Electrical signals attendant to the depolarization and re-polarization of the heart are transmitted from a tip electrode to control unit 304. In a typical manner of operation, control unit 304, in response to electrical signals received from the tip electrode, applies a supply voltage, $V_{SUPP}$, across conductors 13 and 15 of a pre-established polarity so as to selectively and alternately activate and deactivate sensors 19 and 20 via switch 306. Switch 306 typically senses the presence and polarity of the supply voltage, $V_{SUPP}$.

Note that sensor assembly 17 of the present invention may be employed in both series and parallel electrical configurations in respect of conductors 13 and 15. The multiplexing circuitry described hereinabove has the significant advantage of eliminating the requirement to have three or more conductors in lead 14 when two or more sensors are mounted in sensor assembly 17.

In a different embodiment of the present invention, signals from sensors 19 and 20 are not mulitplexed up conductors 13 and 15. Instead, lead 14 contains 3 electrical conductors, where the first two conductors are electrically insulated from one another and connected separately to sensors 19 and 20, while the third conductor serves the ground conductor.

In one such embodiment of the present invention consistent with sensor assembly 17 illustrated in FIGS. 12(a) through 24, first and second conductors are co-axially disposed to a first side of the center of the lead body of lead 14 as seen in cross-section, while a third conductor is disposed to an opposite diametrically opposed second side of the lead body of lead 14 as seen in cross-section. The distal end of the inner first conductor is then electrically coupled to feedthrough pin 270, which in turn is electrically coupled to first sensor 19, more about which we say below. The distal end of the second conductor is electrically coupled (most preferably by welding) to multiple sensor housing via an adapter assembly (not shown in the drawings of multiple sensor assembly 17 included herein) 166 to thereby function as a case ground wire. The distal end of the third conductor is electrically coupled to feedthrough pin 272, which in turn is electrically coupled to second sensor 20.

In FIGS. 12(a), 12(b), 13(a), 13(b), 13(c), 13(d), 21, 22 and 23 there are shown first longitudinally oriented imaginary plane 294 and longitudinally oriented imaginary axis 296. Imaginary axis 296 is preferably, although not necessarily, coincident with an imaginary longitudinal axis that is centrally disposed respecting housing 166 and sensor assembly 17. First longitudinally oriented imaginary plane 294 most preferably intersects imaginary axis 296, and further has first elongated housing member 168 disposed to a first side thereof and second elongated housing member 170 disposed to a second side thereof, the second side being opposite from the first side. Note, however, that elongated housing member 168 or 170 may be shaped or configured such that at least portions thereof are disposed to the first and second sides of imaginary plane 294. Likewise, imaginary plane 294 need not intersect imaginary axis 296.

Additionally, note that the scope of the present invention is not limited merely to embodiments where sensor assembly 17 comprises two elongated housing members only that essentially form two "half-shell" housings. Instead, and as illustrated in FIGS. 25 and 26, sensor assembly 17 may comprise three, four or more elongated housing members having their major axes parallel or substantially parallel to imaginary axis 296.

FIG. 25, for example, shows sensor assembly 17 comprising three elongated housing members, each elongated housing member most preferably containing a separate sensor assembly. The three elongated housing members in FIG. 25 are first elongated housing member 168, second elongated housing member 170 and third elongated housing member 169. In a preferred embodiment of the present invention, the respective spatial volumes occupied by three elongated housing members 168, 169 and 170 are defined by first, second and third triaxial longitudinally oriented imaginary planes 320, 322 and 324 which intersect imaginary axis 296 and also third longitudinal housing seam 285, second longitudinal housing seam 286 and first longitudinal housing seam 284, respectively.

First triaxial imaginary plane 320 most preferably has second elongated housing member 168 disposed to a first side thereof and third elongated housing member 169 disposed to a second side thereof, the second side being opposite from the first side. Note, however, that elongated housing members 168, 169 or 170 may be shaped or configured such that at least portions thereof are disposed to the first and second sides of any of triaxial imaginary planes 320, 322 and 324. Likewise, none of imaginary planes 320, 322 and 324 need intersect imaginary axis 296.

FIG. 26 shows sensor assembly 17 having first, second, third and fourth elongated housing members 168, 170, 169 and 171, respectively. Each of elongated housing members 168, 170, 169 and 171 most preferably contains a separate sensor assembly. In a preferred embodiment of the present invention, the respective spatial volumes occupied by four elongated housing members 168, 170, 169 and 171 are defined by first and second longitudinally oriented imaginary planes 294 and 295 which most preferably intersect imaginary axis 296 as well as first, second, third and fourth longitudinal housing seams 284, 286, 285 and 287, respectively.

First imaginary plane 294 most preferably has first and second elongated housing members 168 and 170 disposed to a first side thereof and third and fourth elongated housing members 169 and 171 disposed to a second side thereof, the second side being opposite from the first side. Note, however, that elongated housing members 168, 169, 170 and 171 may be shaped or configured such that at least portions thereof are disposed to the first and second sides of imaginary plane 294. Likewise, imaginary plane 294 need not intersect imaginary axis 296. Second imaginary plane 295 most preferably has first and third elongated housing members 168 and 169 disposed to a first side thereof and second and fourth elongated housing members 170 and 171 disposed to a second side thereof, the second side being opposite from the first side. Note, however, that elongated housing members 168, 169, 170 and 171 may be shaped or configured such that at least portions thereof are disposed to the first and second sides of imaginary plane 295. Likewise, imaginary plane 295 need not intersect imaginary axis 296.

Figure 12A:
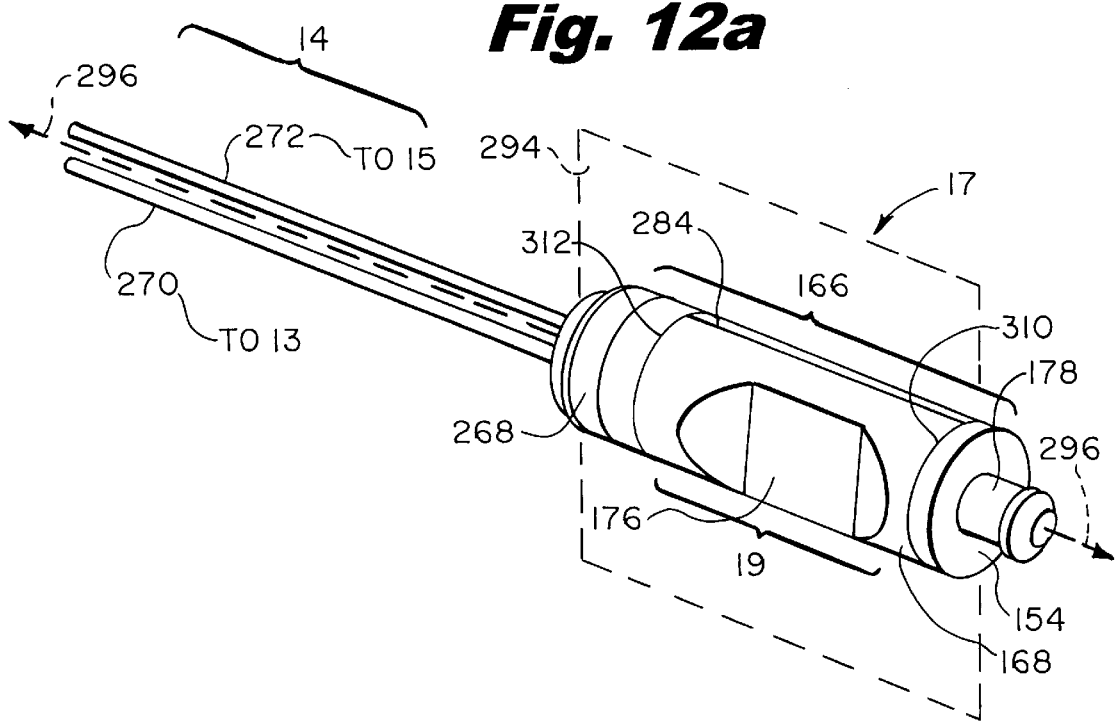
FIGS. 12(a) and 12(b) show different perspective views of one embodiment of a sensor assembly of the present invention.
Figure 12B:
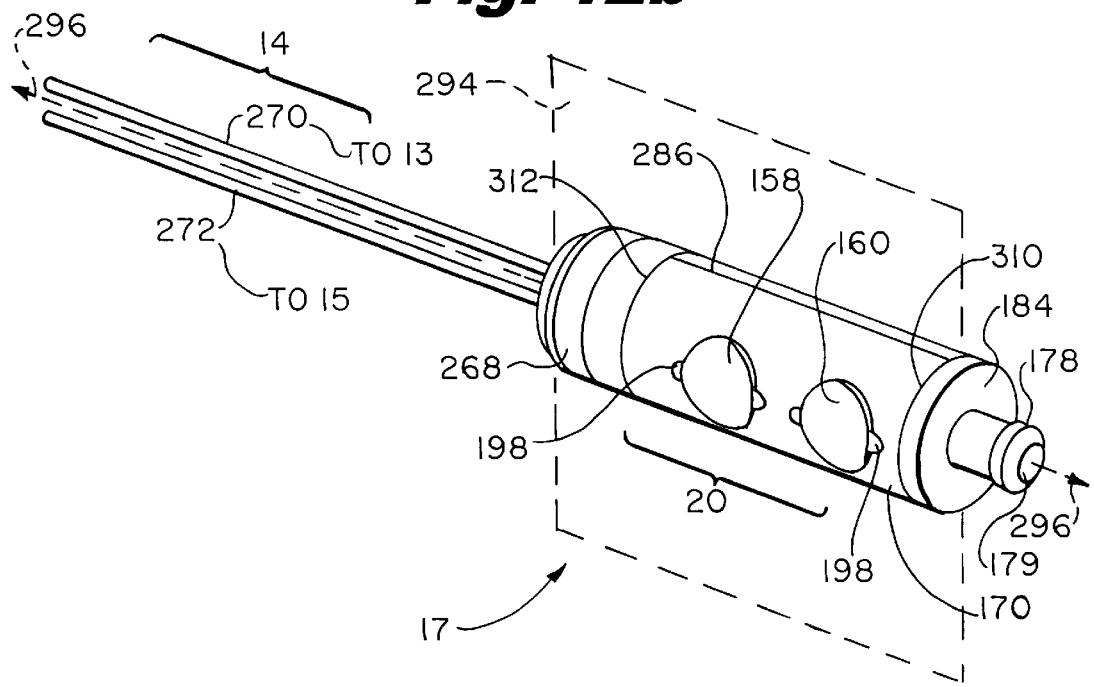

FIGS. 12(a) and 12(b) show perspective views of two different sides of one embodiment of multiple sensor assembly 17 of the present invention. FIG. 12(a) shows a left perspective view multiple sensor assembly 17. FIG. 12(b) shows a right perspective view of multiple sensor assembly 17. FIGS. 13(a) through 13(c) show side and end views of the embodiment of the present invention shown in FIGS. 12(a) and 12(b). In the embodiment of the present invention shown in FIGS. 12(a) through 24, multiple sensor housing 166 comprises two elongated longitudinally-oriented housing members 168 and 170.

Note that multiple sensor assembly 17 may or may not include a lumen, space or other provision for permitting a stylet to pass therethrough to or near tip 27 of lead 14. Sensor assembly 17 may include, for example, a space, channel, tube or lumen for accepting or passing a stylet through housing 166 to tip 27 of lead 14. Additionally, it is preferred that housing 166 be formed at least partially from electrically conductive material such as titanium and thus may be employed as an electrode (either an anode or a cathode), or alternatively may be adapted for use as an electrical through-conductor.

Note further that first sensor 19 need not be a pressure sensor, but instead may be any type of sensor suitable for measuring physiologic parameters in a patient's heart or the blood passing therethrough. Likewise, second sensor 20 need not be an oxygen sensor, but instead may be any type of sensor suitable for measuring physiologic parameters in a patient's heart or the blood passing therethrough. Examples of sensors other than relative pressure, absolute pressure or oxygen saturation finding particularly efficacious application in the present invention include, but are not limited to, pH sensors, temperature sensors (usually thermistors), and $pCO_2$ (partial pressure of $CO_2$ gas) sensors.

Continuing to refer to FIGS. 12(a) through 13(c), elongated housing members 168 and 170 each most preferably comprise separate sensor assemblies for implantably measuring one or more physiologic parameters of a mammalian subject (usually a human being), such as oxygen saturation levels, absolute pressure, relative pressure, carbon dioxide concentration, and the like. Elongated housing members 168 and 170 most preferably have disposed and mounted within them their respective physiologic sensor assemblies, the at least two physiologic sensor assemblies being arranged in a back-to-back, diametrically opposed or mechanical parallel configuration (as opposed to a conventional end-to-end or mechanical series configuration).

One preferred material for forming elongated housing members 168, 169, 170 and 171, adapter sleeve 268, tip segment attachment member 178, and ferrules 154 and 156 is electrically conductive commercial grade 1 or 2 titanium or titanium alloy, although other materials may be substituted therefor. Examples of other suitable materials include, but are not limited to commercial grade 3, 4, or 5 titanium or titanium alloy, stainless steel, platinum, niobium, and the like. Elongated housing members 168, 169, 170 and 171, adapter sleeve 268, longitudinal housing seams 284, 285, 286 and 287, proximal housing seam 312 and distal housing seam 310 are most preferably laser welded together once sensor assembly 17 has been assembled using techniques well known in the art.

Tip segment attachment member 178 is attached to the distal end of housing 166 and is likewise most preferably formed of electrically conductive titanium. Tip segment attachment member 178 may or may not include a channel, groove, tube, space, recess or other provision for a stylet to pass therethrough to tip 27 of lead 14, and may further be configured to cooperate with a stylet or conductor lumen of the type shown in FIGS. 18 and 19 as lumen 326.

Adapter sleeve 268 is attached to the proximal end of housing 166, and like tip segment attachment member 178 is most preferably formed of electrically conductive titanium. Thus, housing 166, first elongated housing member 168, second elongated housing member 170 and tip segment attachment member 178 are most preferably electrically and mechanically coupled to one another such that they remain at the same ground electrical potential. Tip segment attachment member 178 may also be formed of a polymeric material and may further be shaped to have gradually sloping or tapered outer surfaces to ease insertion of lead 14 within the venous or arterial systems, or within the heart.

In a preferred embodiment of the present invention, tip segment attachment member 178 has tip segment recess 179 for receiving therewithin a short crimp core or rod-shaped member (not shown in the figures) which is preferably metallic and electrically conductive. The crimp core is first placed within tip segment recess 179, the proximal end of the coiled electrode conductor (also not shown in the Figures) is placed between the outer surface of the crimp core and the inner surface of tip segment attachment member 178, and the outer surface of tip segment attachment member 178 is compressed such that the inner surface of member 178 disposed within recess 179 crimpingly engages proximal portions of the coiled electrode conductor against the crimp core and tip attachment member 178. The resulting coiled electrode conductor extends distally from assembly 17 towards distal tip 27 of lead 14 for attachment to a tip electrode, and is further electrically connected to housing 166.

First sensor 19 (shown in the Figures as an absolute pressure sensor) most preferably comprises a diaphragm 176, in turn most preferably formed of thin titanium metal. Diaphragm 176 is capable of deflecting in response to pressure being applied thereto, forms a first plate of a capacitor, and is optimally about 0.001 inches in thickness. Beneath diaphragm 176 there is positioned a pressure measurement ceramic hybrid 188 having a second plate of the capacitor formed thereon, the capacitance of the capacitor changing in some proportion or predictable manner according to the distance between the first and second plates. The preferred distance 266 between the underside of diaphragm 176 and the second plate is about 0.0005 inches or less. As the capacitance of the capacitor changes in response to deflection of diaphragm 176, so too does the oscillation frequency output by a capacitance measurement circuit included in pressure measurement ceramic hybrid 188.

Examples of an absolute pressure sensor adaptable for use in accordance with the present invention are disclosed in U.S. Pat. Nos. 5,535,752 and 5,564,434 to Halperin et al.

First and second optical lenses 158 and 160 of second sensor 20 (shown in the Figures as an oxygen saturation level sensor) are mounted in second elongated housing member 170. As shown in further detail in FIGS. 13(*d*) and 14, first and second lenses 158 and 160 of sensor 20 are most preferably mounted in first and second lens openings 150 and 152 on first and second lens ferrules 154 and 156, respectively.

Lenses 158 and 160 are most preferably manufactured using biocompatible and biostable materials suitable for long-term placement within the blood of a patient, such as sapphire, aluminum oxide grown with a single crystal lattice structure, ruby and glass. Sapphire may be easily cut and polished to optical clarity without creating defects or cracks. If cracks or defects are present in the sapphire, they may be detected readily at low magnification. Sapphire is also biocompatible and biostable, even under long-term exposure conditions in a blood environment.

Although sapphire is the preferred material for lenses 158 and 160, it will be understood that lenses 158 and 160 may be provided of any appropriate material that provides the required biocompatible and biostable properties for long-term implantation. When first and second lenses 158 and 160 are employed to transmit and receive optical energy, the material from which lenses 158 and 160 are fabricated should transmit and receive optical energy over desired wavelength bands.

Note further that lenses 158 and 160 shown in FIGS. 12(*a*) through 13(*b*) have preferred curved outer surfaces conforming generally to the corresponding shape and curvature of the outer surface of housing 170. Contrariwise, and in another embodiment of the present invention, lenses 158 and 160 shown in FIGS. 22 through 24 have less desirable flat or substantially flat outer surfaces.

Continuing to refer to FIGS. 12(*a*) through 14, attachment of ferrules 154 and 156 and lenses 158 and 160 within the window openings 50 and 152 in elongated housing member 170 is typically accomplished by welding ferrules 1554 and 152 in place. Such welding is typically performed using a laser beam directed near interfaces 173 and 175 of ferrules 154 and 156 and adjoining surfaces of elongated housing member 170 to form a hermetic seal between ferrules 154 and 156 and elongated housing member 170. Other welding processes, including but not limited to electron beam welding, may also be employed to weld ferrules 154 and 156 in place.

First and second ferrules 154 and 156 preferably include bodies having lens opening 150 and 152 in which lenses 158 and 160 are located. Lens openings 150 and 152 are surrounded by first and second lens flanges 172 and 174 which locate lenses 158 and 169 in their proper positions in respect of ferrules 154 and 156. After lenses 158 and 160 are placed in position within ferrules 154 and 156, they are preferably maintained within ferrules 154 and 156 by brazing. Brazing material is preferably employed to form fillets around the peripheries of lenses 158 and 160. Brazing material also may wick between lenses 158 and 160 ferrules 154 and 156.

Brazing material preferably forms an hermetic seal between lenses 158 and 160 and ferrules 154 and 156. As a result, optical lens assembly 162 according to the present invention provides multiple hermetically sealed optical lenses for implantable medical electrical lead 14 by virtue of the hermetic seals disposed between elongated housing member 170 and ferrules 154 and 156, and the hermetic seal disposed ferrules 154 and 156 and lenses 158 and 160. Brazing material employed to connect lenses 158 and 160 to ferrules 154 and 156 may be composed of any suitable biocompatible or biostable materials such as gold and gold alloys. One exemplary brazing material is gold having a purity of about 99.9%.

When pure gold brazing material is employed, lenses 158 and 160 when formed of sapphire must first be provided with a coating of niobium, titanium, or a niobium/titanium alloy, as well as with a coating of a gold disposed over the niobium or titanium in areas where brazed joints are to be formed. Various proportions of niobium and titanium may be co-sputtered to form the desired layer of a niobium/titanium alloy. These and other considerations regarding the brazing of sapphire lenses to ferrules are discussed in International Publication No. WO 80/01620, hereby incorporated by reference herein in its entirety.

Ferrules 154 and 156 also preferably include braze stops adapted to prevent brazing material from flowing over undesired portions of ferrules 154 and 156. Such braze stops typically assume a corner shape or other sharp discontinuity in the outwardly facing surfaces of ferrules 154 and 156 upon which brazing material is disposed. Such discontinuities prevent brazing material from flowing into undesired areas owing to surface tension inherent in the flowable brazing material employed during the brazing process.

As best shown in FIG. 13(*d*), ferrules 154 and 156 most preferably include support flanges 155 and 157 disposed about the outer peripheries of ferrules 154 and 156. Support flanges 155 and 157 rest against the peripheries of window openings 150 and 152 in elongated housing member 170 to accurately locate ferrules 154 and 156 with respect to housing member 170 for the welding process described above. Ferrules 154 and 156 also most preferably include U-shaped strain relief channels 159 and 161. By providing such channels, residual stresses, primarily occurring in tensional modes that might otherwise be present in ferrules having no strain relief channels, are reduced or eliminated by those stresses into bending strains which U-shaped channels 159 and 161 accommodate.

As shown in FIG. 13(*c*), tip attachment member 178 most preferably includes vent hole 184 for evacuating gas from the interior of housing 166 or pulling a vacuum thereon. FIG. 13(*b*) shows adhesive fillports 198 within which medical grade silicone or siloxane adhesive may be disposed while pulling a vacuum on the interior of housing 166 through vent hole 184 to thereby suck the adhesive into and around lenses 158 and 160, as well as around ferrules 154 and 156. It is preferred to wait until all other seams and holes in sensor assembly 17 are welded shut or otherwise sealed before pulling a vacuum of less than 1 Torr on housing 166 for a duration lasting overnight, and to then backfill housing 166 with helium to both remove moisture from the interior of housing 166 as well as to drive volatiles out of the medical grade adhesives employed in constructing and assembling sensor assembly 17.

FIGS. 13(*d*) and 15 show feedthrough assembly 182 comprising feedthrough ferrule 180, feedthrough insulator 260, first feedthrough pin 270 and second feedthrough pin 272. Adapter sleeve 268 fits over and engages the proximal end of feedthrough ferrule 180. Feedthrough insulator 260 is most preferably formed of sapphire-containing ceramic, but may alternatively be formed of any suitable feedthrough glass or ceramic composition capable of forming an hermetic seal, many of which are well known in the art. The proximal ends of feedthrough pins 270 and 272 are joined to conductors 13 and 15, respectively, of lead 14, most preferably by staking or crimping sleeve means.

Referring now to FIGS. 13(d) and 18 through 22, in a preferred embodiment of the present invention lens 158 covers an emitter portion 264 of sensor 20 while lens 160 covers a detector portion 262 of sensor 20. Emitter portion 264 most preferably comprises first and second light emitters 192 and 194, one of which most preferably emits light in the red light wavelength spectrum, the other of which most preferably emits light in the infra-red light wavelength spectrum. Detector portion 262 most preferably comprises light detector 195. Light detector 195 may be, for example, a PIN diode.

At least portions of light barrier 280 are most preferably disposed between emitter portion 264 and detector portion 262 to form, most preferably, but not necessarily, in cooperation with elongated housing member light barrier 151 and/or portions of second elongated housing member 170, a light barrier between emitter portion 264 and detector portion 262. As discussed hereinabove, such a structure prevents light emitted by light emitters 192 and 194 from scattering or reflecting internally within elongated housing member 170 or housing 166 such that spurious undesired light beams impinge upon detector portion 262.

In preferred embodiments of the present invention, light barrier 280 is formed of silicone molded 75D containing titanium oxide as a light-reflective filler. Surfaces 281 of light barrier 280 may or may not be reflective, however, and may or may not be shaped or sloped to collimate or reflect outwardly sideways-emitted light emanating from light emitters 192 and 194. Surfaces 281 may be slanted, sloped or parabolically shaped, for example, to more efficiently collimate and direct light emanating from light emitters 192 and 194 outwardly through lens 158. Surfaces 282 may also be coated with highly reflective material such as foil or polished metal to more efficiently reflect backscattered, backwardly directed or sideways-directed light beams towards or through lens 158.

FIGS. 28(a) and 28(b) show alternative embodiments of light barrier 280 of the present invention suitable for use in single "tube" or single lens oxygen sensors as well as in dual lens oxygen sensors. Both embodiments of the present invention illustrated in FIGS. 28(a) and 28(b) utilize adjoining layers of lenses 158 or 160 having differing indices of refraction to achieve the same result, namely directing light rays passing through lenses 158 and 160 such that internal reflection or refraction within lens 158 is lessened or eliminated. In accordance with this embodiment of light barrier 280 of the present invention, light rays emitted by light emitters 192 or 194 cannot refract or reflect internally within lens 158 for transmission to light detector portion 262 and eventual spurious detection by light detector 195.

Referring now to FIG. 28(a), there is shown refractive coating 282 applied to the inner surface of lens 158. Coating 282 shown in FIG. 28(a) has a higher index of refraction than does lens 158, and therefore bends light emanating from light emitter 192 or 194 toward the surface normal, thereby preventing light incident upon the boundary between the outer surface of lens 158 and blood mass 167 from reaching the critical angle of incidence required for total internal reflection.

The relationship between angles of incidence relative to the surface normal may be characterized by Snell's Law. Snell's Law states that a refracted light path is proportional to the speed of light in different media. In other words, the index of refraction of a first medium times the sine of its angle of incidence thereon is equal to the index of refraction of the second medium times the angle of the refracted ray relative to the surface normal. This concept is illustrated in FIG. 28(a), where coating 282 has an index of refraction greater than that of lens 158.

In another embodiment of light barrier 280 of the present invention, an anti-reflective coating 283 is disposed on the inner surface of lens 158. Coating 283 most preferably has an optical thickness of one-fourth of the wavelength of the light incident thereon. It is preferred that coating 283 be formed of a dielectric material. As illustrated in FIG. 28(b), coating 283 results in destructive interference between light reflected from a first surface and that reflected from a second surface. The index of refraction required for coating 283 may be determined by taking the square root of the index of refraction of lens 158 (most preferably formed of sapphire), assuming that free space is disposed inside light emitter portion 264. As an example, sapphire has an index of refraction N equal to 1.33, and thus coating 283 may be formed of magnesium fluoride (having an index of refraction N=1.38) or lithium fluoride (where N=1.38). Coating 283 has an index of refraction less than that of lens 158.

Figure 16:
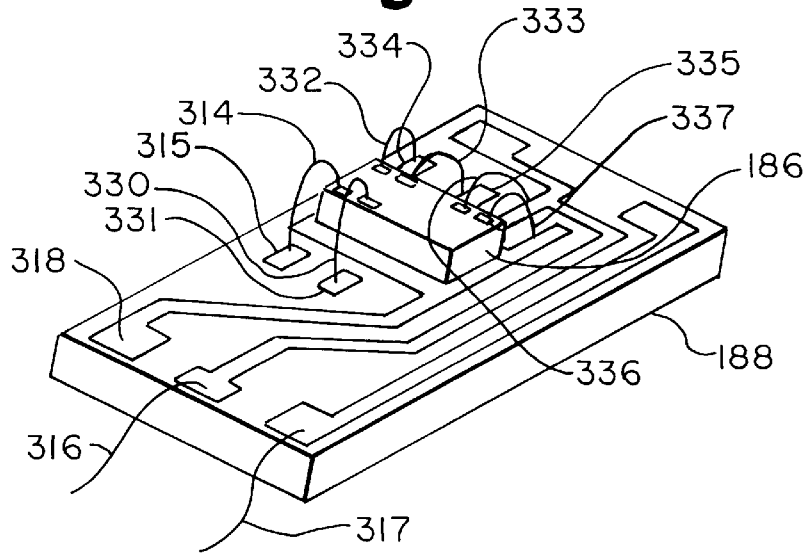
FIG. 16 shows a pressure sensor hybrid of one embodiment of the present invention.
Figure 17:
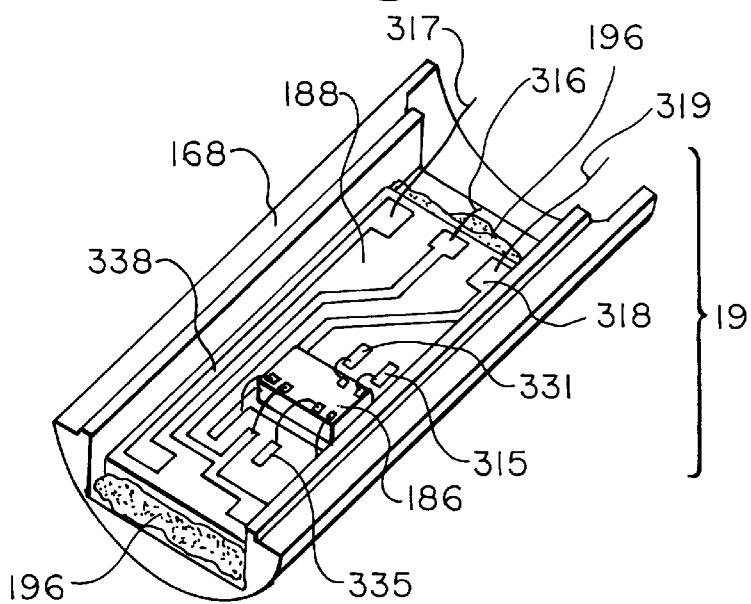
FIG. 17 shows the pressure sensor hybrid of FIG. 9 mounted in an elongated housing member of the present invention.

We refer now to FIGS. 13(d) and 16 through 22, where there is shown one embodiment of sensor assembly 17 of the present invention and its associated sensor hybrids 188 and 190. FIGS. 16 and 17 show pressure sensor hybrid 188 as including pressure sensor IC 186, which in a preferred embodiment of the present invention has an oscillator circuit for charging two capacitors disposed on the underside of hybrid 188 in close proximity to pressure sensor diaphragm 176. Electrical conductor 314 connects the first capacitor of sensor 19 to IC 186 through wirebond contact pad 315, and is most preferably formed of aluminum wire. Electrical conductor 332 connects the second capacitor of sensor 19 to IC 186 through wirebond contact pad 334, and is likewise most preferably formed of aluminum wire. Electrical conductor 330 connects IC 186 to a first shield circuit disposed on or near the underside of pressure sensor hybrid 188, the first shield circuit reducing the parasitic capacitance associated with circuitry for the first capacitor, and being connected to IC 186 through wirebond contact pad 331. Electrical conductor 333 connects IC 186 to a second shield circuit disposed on or near the underside of pressure sensor hybrid 188, the second shield circuit reducing the parasitic capacitance associated with circuitry for the second capacitor, and being connected to IC 186 through wirebond contact pad 335. Electrical conductors 330 and 33 are most preferably formed of aluminum wire.

Pressure sensor IC 186 most preferably has two inputs: a first input signal corresponding to the degree of deflection of diaphragm 176 and a second input signal corresponding to a different variable unrelated to pressure, typically temperature. Pressure sensor IC 186 then utilizes the first and second input signals to determine a more reliable estimate of absolute pressure through common mode error cancellation. In such a manner, errors arising from changes in temperature, changes in the characteristics of the oscillator circuit of pressure sensor IC 186, changes in the dielectric characteristics of the air disposed in the gap between the first and second plates of the capacitor, and other changes may be compensated for.

Electrical conductor 316 connects portions of hybrid 188 to case or ground, and is most preferably formed of gold wire. It is preferred to connect conductor 316 to the case or ground with electrically conductive epoxy and its corresponding wirebond pad by wirebonding. Element 318 is a wirebond contact pad. In FIG. 10, electrical conductor 319 connects feedthrough pin 270 to pressure sensor hybrid 188, and is most preferably formed of gold wire. Adhesive 196 preferably attaches at least portions of the ends of hybrid 188 to at least portions of the interior surfaces of elongated housing member 168, and most preferably comprises medical grade silicone or siloxane. Electrical conductor 317 connects the distal end of feedthrough pin 272 to oxygen sensor hybrid 190 via through-conductor 338 disposed on the upper surface of pressure sensor hybrid 188, and is most preferably formed of gold wire. Electrical conductor 319 connects the distal end of feedthrough pin 270 to pressure sensor hybrid 188, and is also most preferably formed of gold wire.

Figure 18:
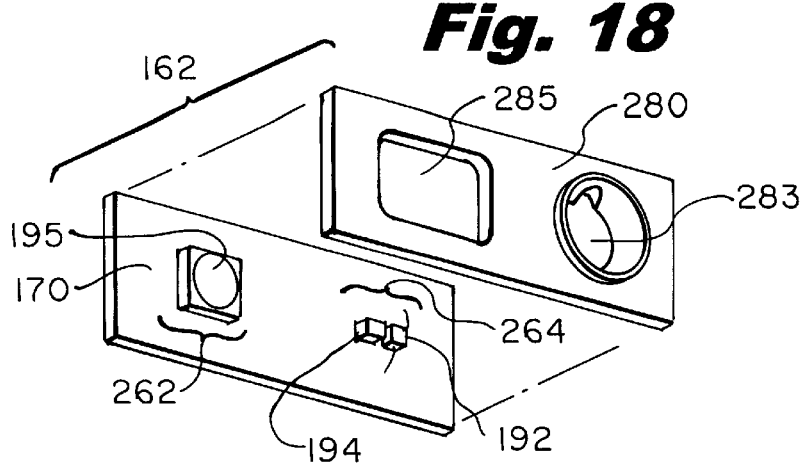
FIG. 18 shows an exploded perspective view of one embodiment of an oxygen sensor hybrid and corresponding light barrier of the present invention.
Figure 19:
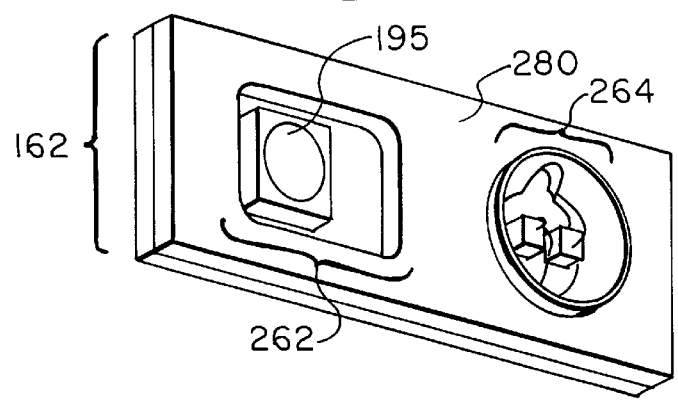
FIG. 19 shows a perspective view of the assembled oxygen sensor hybrid and corresponding light barrier of FIG. 18.
Figure 20:
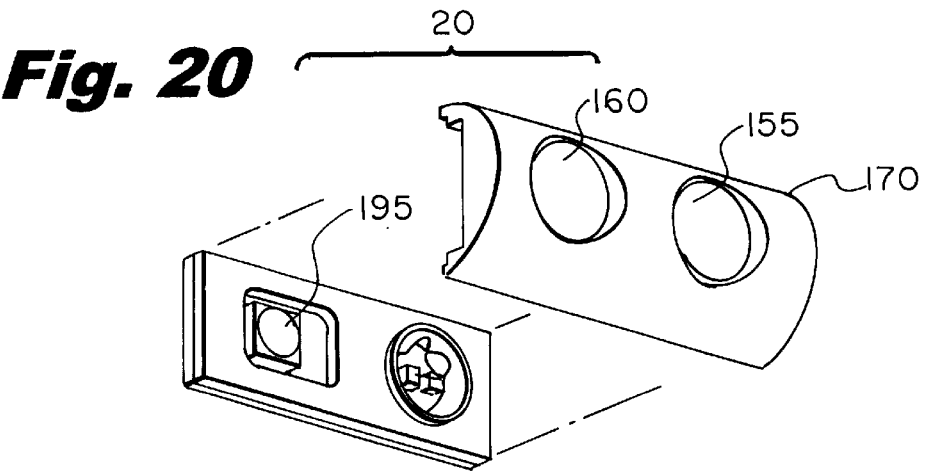
FIG. 20 shows an exploded perspective view of the assembled oxygen sensor hybrid and corresponding light barrier of FIG. 19 and a corresponding second elongated housing member.
Figure 23:
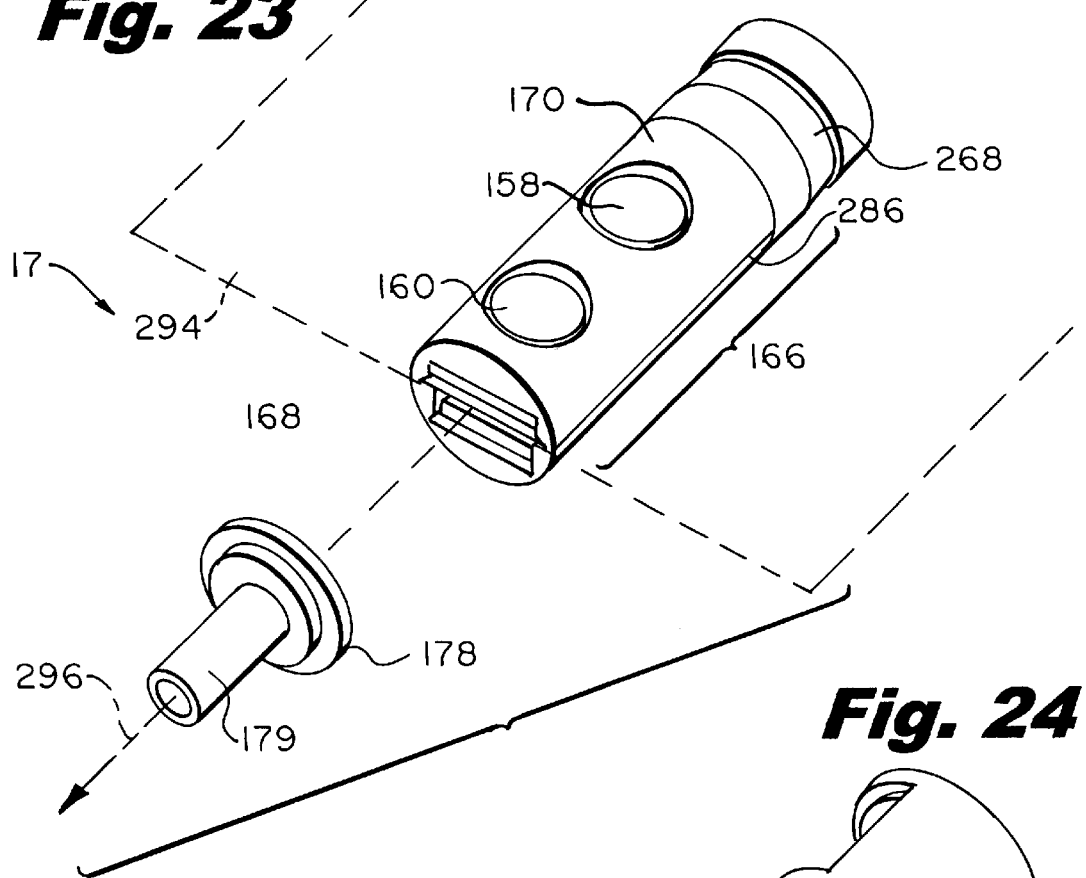
FIG. 23 shows a partially exploded perspective view of the elongated housing members of FIG. 22 and a tip segment attachment member of the present invention.
Figure 24:
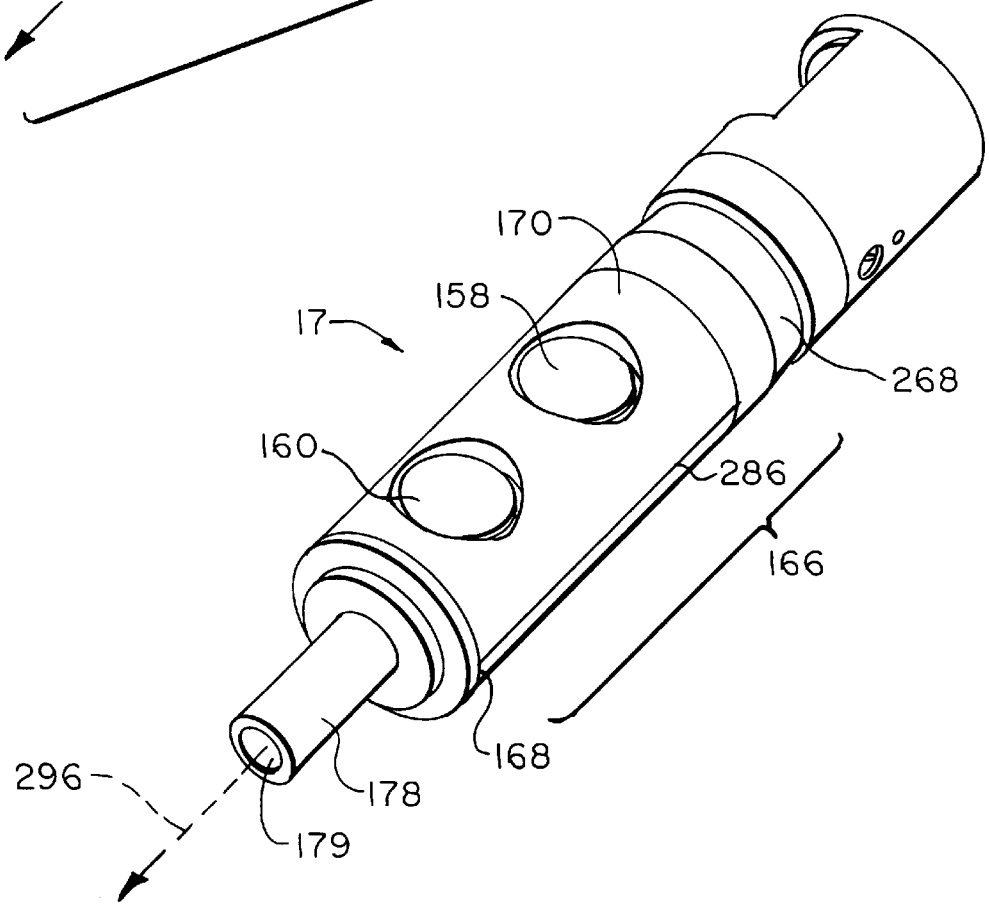
FIG. 24 shows the elongated housing members and tip segment attachment member of FIG. 23 in an assembled state.
Figure 27A:
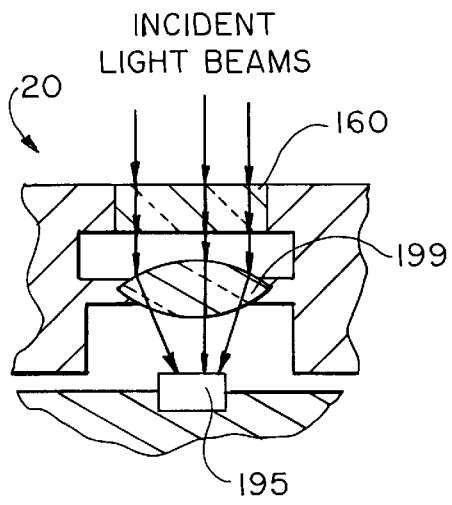
FIGS. 27(a) through 27(d) show various embodiments of the light focusing device and corresponding light detector of the present invention.
Figure 27B:
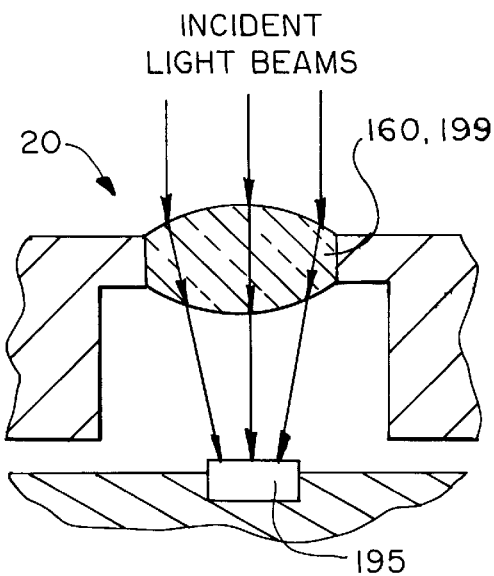
Figure 27C:
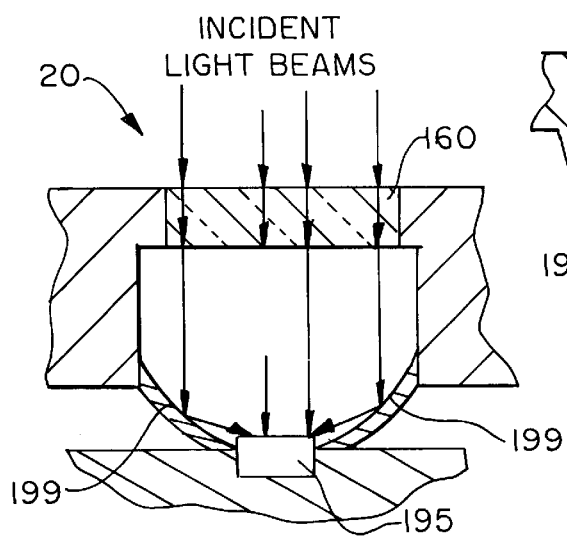
Figure 27D:
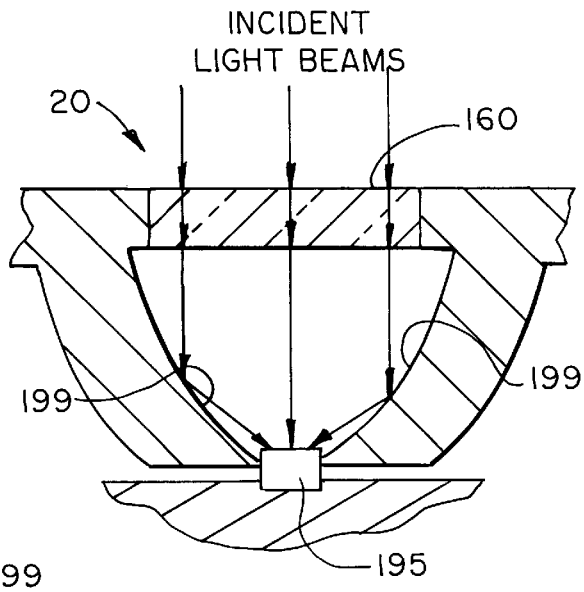

FIGS. 18 through 20 show various components included in optical sensor assembly 162. Light emitters 192 and 194 are mounted on oxygen sensor hybrid 190 and together form a part of light emitter portion 264. Light detector 195 is mounted on oxygen sensor hybrid 190 and forms a part of light detector portion 262. Gasket or barrier 280 has openings 283 and 285 disposed therein for permitting light emitted by light emitters 192 and 194 to pass through lens 158 and for permitting light reflected back through lens 160 to be sensed by light detector 195. Sensor 20 comprises oxygen sensor hybrid 190, light detector portion 262, light emitter portion 264, light barrier or barrier 280, elongated housing member 170 and lenses 158 and 160. Note that the embodiment of light barrier 280 of the present invention shown in FIGS. 18 through 20 does not include sloped surfaces 281 for collimating, reflecting or directing sideways or backwardly-directed light emitted from light emitters 192 and 194 towards lens 158.

FIG. 21 shows oxygen sensor 20 and pressure sensor 19 of FIGS. 16 through 20 in a partially assembled state. Integrated circuit 191 is mounted on oxygen sensor hybrid 190, and processes signals relating to the determination of blood oxygen saturation. Thin film resistor 288 on hybrid 190 is most preferably trimmable to permit the frequency at which an oscillator circuit operates to be adjusted or tuned, at least portions of the oscillator circuit most preferably being incorporated into integrated circuit 191. FIG. 22 shows sensors 19 and 20 in an assembled state to form housing 166.

Referring now to FIGS. 27(a) through 27(d), there is shown another embodiment of the present invention where light focusing device 199 increases the efficiency and efficacy of light detector 195. As shown in FIGS. 27(a) through 27(d), light focusing device 199 may assume the form of a focusing lens disposed between light detector 195 and lens 160, a reflector disposed near light detector 195, a focusing portion of lens 160, or reflective and appropriately shaped and configured sidewalls positioned to gather and reflect light towards light detector 195. Light focusing device 199 is thus positioned in or on the second lens or inside the housing within which light detector 195 is located. Light focusing device 199 gathers light transmitted through lens 160 into such housing, and further guides the light so gathered to light detector 195 for more efficient detection thereby.

When light focusing device 199 is a reflector, device 199 may assume any of a number of different configurations, such as parabolically shaped reflectors, spherically shaped reflectors, curved reflectors and flat reflectors. In the case where device 199 is a parabolic or elliptical reflector, light detector 195 is ideally positioned near or at the appropriate focus thereof. When light focusing device 199 is a lens, the lens most preferably is configured to refract and focus light beams transmitted therethrough to light detector 195. When light focusing device 199 is at least one sidewall, the at least one sidewall is most preferably disposed between light detector 195 and lens 160 and forms an at least partially reflective surface. Light focusing device 199 finds application in the two lens oxygen sensors disclosed herein, as well as in the single lens or sapphire tube oxygen sensors of the prior art.

The sensors discussed hereinabove with reference to FIGS. 1 through 28(b) have been described in a generic manner, since it is intended that any suitable implantable physiologic sensor may be incorporated as part of a sensor assembly according to the present invention. The following list of sensor types is provided to illustrate various known implantable physiologic sensors that are well suited for incorporation into a sensor assembly of the present invention. It is to be understood that this non-exhaustive list of sensor types is provided for illustrative purposes only, and is not intended to limit the type of sensor that may be employed in conjunction with the present inventions disclosed herein.

Such sensors include, but are not limited to, capacitive absolute pressure sensors; optical based oxygen saturation sensors; piezo-resistive absolute pressure sensors; relative pressure sensors; acceleration or activity sensors; electro-chemical sensors, such as oxygen sensors and glucose sensors; Doppler flow sensors; strain gauge sensors; and electronic thermo-dilution sensors.

As discussed hereinabove, in one embodiment of the present invention sensor assembly 17 includes a pressure sensor 19 and an oxygen saturation sensor 20. An exemplary capacitive absolute pressure sensor well suited for use in sensor assembly 17 is described in U.S. Pat. Nos. 5,535,752 and 5,564,434, both of which are issued to Halperin et al. and incorporated herein by reference in their respective entireties. It should be noted that the capacitive absolute pressure sensor disclosed in U.S. Pat. Nos. 5,535,752 and 5,564,434 is a single sensor that monitors two distinct physiologic parameters, namely, an absolute blood pressure parameter and a blood temperature parameter.

As discussed hereinabove, sensor assembly 17 may include pressure sensor 19 in combination with oxygen sensor 20. An exemplary oxygen saturation sensor well suited for use in sensor assembly 17 is described in U.S. Pat. Nos. 4,750,495 and 4,903,701, both of which are issued to Moore et al. and incorporated herein by reference in their respective entireties.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to use of a sensor assembly in conjunction with a particular implantable medical device, such as a pacemaker, but may be used in conjunction with other medical devices as well. The present invention is also not limited to specific data acquisition and communications techniques, such as those presented herein, but such functions may be directed using other like techniques. The present invention further includes within its scope methods of using the sensor assembly as well as the particular structures described hereinabove. In the claims, means-plus-function clauses are intended to cover the structures described herein as performing the recited function and their equivalents. Means plus function clauses are not intended to be limited to structural equivalents only, but are also intended to include structures which function equivalently in the environment of the claimed combination.

All patents and printed publications referenced hereinabove are hereby incorporated by reference into the specification hereof, each in its respective entirety.

What is claimed is:

1. A body implantable medical electrical lead adapted to be implanted in a living body in operative relation with oxygenated body fluid, comprising:
   (a) a lead body having proximal and distal ends and comprising an electrically insulative material;
   (b) at least first and second electrical conductors disposed within at least portions of the lead body, the conductors having at least portions of the electrically insulative material disposed therebetween;
   (c) an oxygen sensor attached to the lead body and coupled electrically with said first and second lead conductors, comprising:
      (i) a housing having proximal and distal ends, an exterior, and first and second interior portions disposed therewithin;
      (ii) a light emitter disposed within the first interior portion of the housing;
      (iii) a light detector disposed within the second interior portion of the housing;
      (iv) a light transmissive first lens disposed over the light emitter and mounted in the housing between the exterior and the first interior portion of the housing to enable at least portions of light emitted by the light emitter to pass through the first lens from the first interior portion to the exterior;
      (v) a light transmissive second lens disposed over the light detector and mounted in the housing between the exterior and the second interior portion of the housing to enable at least portions of light emitted by the light emitter through the first lens and reflecting from oxygenated body fluid adjacent to at least portions of the housing exterior to pass through the second lens from the exterior to the second interior portion, the first and second lenses being separated and spaced apart from one another; and
      (vi) a light barrier positioned between the first interior portion and the second interior portion, the light barrier not permitting light emitted by the light emitter to be transmitted therethrough into the second interior portion for detection by the light detector.

2. The body implantable medical electrical lead of claim 1, wherein the light barrier is further positioned between the first lens and the second lens, the light barrier not permitting light emitted by the light emitter to be transmitted therethrough for detection by the light detector.

3. The body implantable medical electrical lead of claim 1, wherein the light barrier is one of a membrane and a gasket.

4. The body implantable medical electrical lead of claim 1, wherein the light barrier includes one of a membrane and a gasket.

5. The body implantable medical electrical lead of claim 1, wherein the light barrier includes at least a portion of the housing.

6. The body implantable medical electrical lead of claim 1, wherein the housing is elongated.

7. The body implantable medical electrical lead of claim 1, wherein the light barrier includes surfaces configured to guide or reflect light towards the light detector.

8. The body implantable medical electrical lead of claim 7, wherein the surfaces are reflective.

9. The body implantable medical electrical lead of claim 7, wherein the surfaces are shaped to at least one of collimate and reflect outwardly light emitted by the light emitter.

10. The body implantable medical electrical lead of claim 7, wherein the surfaces are shaped to at least one of collimate and reflect outwardly light emitted sideways by the light emitter.

11. The body implantable medical electrical lead of claim 7, wherein the surfaces are least one of one of slanted, sloped and parabolically shaped.

12. The body implantable medical electrical lead of claim 7, wherein the surfaces are coated with highly reflective material.

13. The body implantable medical electrical lead of claim 1, wherein the light barrier includes surfaces configured to guide or reflect light emitted by the light emitter towards the first lens.

14. The body implantable medical electrical lead of claim 13, wherein the surfaces are reflective.

15. The body implantable medical electrical lead of claim 13, wherein the surfaces are shaped to at least one of collimate and reflect outwardly light emitted by the light emitter.

16. The body implantable medical electrical lead of claim 13, wherein the surfaces are shaped to at least one of collimate and reflect outwardly light emitted sideways by the light emitter.

17. The body implantable medical electrical lead of claim 13, wherein the surfaces are least one of one of slanted, sloped and parabolically shaped.

18. The body implantable medical electrical lead of claim 13, wherein the surfaces are coated with highly reflective material.

19. The body implantable medical electrical lead of claim 1, wherein at least portions of the light barrier are formed of silicone.

20. The body implantable medical electrical lead of claim 1, wherein at least one of the first and second lenses comprises one of sapphire, ruby and glass.

21. The body implantable medical electrical lead of claim 1, wherein the housing comprises a metal selected from the group consisting of titanium, stainless steel, platinum, niobium, and alloys or combinations thereof.

22. The body implantable medical electrical lead of claim 1, wherein the lead further comprises at least a first electrode for stimulation of cardiac tissue disposed one of near and at the distal end of the lead body.

23. The body implantable medical electrical lead of claim 22, wherein the oxygen sensor attached to the lead body is disposed proximally of the first electrode.

24. The body implantable medical electrical lead of claim 22, wherein the first electrode is a tip electrode.

25. The body implantable medical electrical lead of claim 22, wherein the lead further includes a second electrode.

26. The body implantable medical electrical lead of claim 25, wherein the second electrode is a ring electrode.

27. An implantable medical device system, comprising:
   (a) an implantable medical device adapted to be implanted in a living body;
   (b) a body implantable medical electrical lead attached to the implantable medical device adapted to be implanted in a living body in operative relation with oxygenated body fluid, the lead comprising:
      (i) a lead body having proximal and distal ends and comprising an electrically insulative material, the proximal end of the lead being attached to the implantable medical device;

(ii) at least first and second electrical conductors disposed within at least portions of the lead body, the conductors having at least portions of the electrically insulative material disposed therebetween;

(iii) an oxygen sensor attached to the lead body and coupled electrically with said first and second lead conductors, comprising:

(1) a housing having proximal and distal ends, an exterior, and first and second interior portions disposed therewithin;

(2) a light emitter disposed within the first interior portion of the housing;

(3) a light detector disposed within the second interior portion of the housing;

(4) a light transmissive first lens disposed over the light emitter and mounted in the housing between the exterior and the first interior portion of the housing to enable at least portions of light emitted by the light emitter to pass through the first lens from the first interior portion to the exterior; and (5) a light transmissive second lens disposed over the light detector and mounted in the housing between the exterior and the second interior portion of the housing to enable at least portions of light emitted by the light emitter through the first lens and reflecting from oxygenated body fluid adjacent to at least portions of the housing exterior to pass through the second lens from the exterior to the second interior portion, the first and second lenses being separated and spaced apart from one another; and (6) a light barrier positioned between the first interior portion and the second interior portion, the light barrier not permitting light emitted by the light emitter to be transmitted therethrough into the second interior portion for detection by the light detector.

28. The implantable medical device system of claim 27, wherein the implantable medical device is selected from the group consisting of a heart monitor, a therapy delivery device, a pacemaker, an implantable pulse generator, a pacer-cardio-defibrillator, an implantable cardio-defibrillator, a cardiomyo-stimulator, a nerve stimulator, a brain stimulator, a gastric stimulator and a drug delivery device.

29. The implantable medical device system of claim 27, wherein the light barrier is further positioned between the first lens and the second lens, the light barrier not permitting light emitted by the light emitter to be transmitted therethrough for detection by the light detector.

30. The implantable medical device system of claim 27, wherein the light barrier is one of a membrane and a gasket.

31. The implantable medical device system of claim 27, wherein the light barrier includes one of a membrane and a gasket.

32. The implantable medical device system of claim 27, wherein the light barrier includes at least a portion of the housing.

33. The implantable medical device system of claim 27, wherein the housing is elongated.

34. The implantable medical device system of claim 27, wherein the light barrier includes surfaces configured to guide or reflect light towards the light detector.

35. The implantable medical device system of claim 34, wherein the surfaces are reflective.

36. The implantable medical device system of claim 34, wherein the surfaces are shaped to at least one of collimate and reflect outwardly light emitted by the light emitter.

37. The implantable medical device system of claim 34, wherein the surfaces are shaped to at least one of collimate and reflect outwardly light emitted sideways by the light emitter.

38. The implantable medical device system of claim 34, wherein the surfaces are least one of one of slanted, sloped and parabolically shaped.

39. The implantable medical device system of claim 34, wherein the surfaces are coated with highly reflective material.

40. The implantable medical device system of claim 27, wherein the light barrier includes surfaces configured to guide or reflect light emitted by the light emitter towards the first lens.

41. The implantable medical device system of claim 40, wherein the surfaces are reflective.

42. The implantable medical device system of claim 40, wherein the surfaces are shaped to at least one of collimate and reflect outwardly light emitted by the light emitter.

43. The implantable medical device system of claim 40, wherein the surfaces are shaped to at least one of collimate and reflect outwardly light emitted sideways by the light emitter.

44. The implantable medical device system of claim 40, wherein the surfaces are least one of one of slanted, sloped and parabolically shaped.

45. The implantable medical device system of claim 40, wherein the surfaces are coated with highly reflective material.

46. The implantable medical device system of claim 27, wherein at least portions of the light barrier are formed of silicone.

47. The implantable medical device system of claim 27, wherein at least one of the first and second lenses comprises one of sapphire, ruby and glass.

48. The body implantable medical electrical lead of claim 27, wherein the housing comprises a metal selected from the group consisting of titanium, stainless steel, platinum, niobium, and alloys or combinations thereof.

49. The implantable medical device system of claim 27, wherein the lead further comprises at least a first electrode for stimulation of cardiac tissue disposed one of near and at the distal end of the lead body.

50. The implantable medical device system of claim 49, wherein the oxygen sensor attached to the lead body is disposed proximally of the first electrode.

51. The implantable medical device system of claim 49, wherein the first electrode is a tip electrode.

52. The implantable medical device system of claim 49, wherein the lead further includes a second electrode.

53. The implantable medical device system of claim 52, wherein the second electrode is a ring electrode.

54. A body implantable medical oxygen sensor adapted to be implanted in a living body in operative relation with oxygenated body fluid, comprising:

(a) a housing having proximal and distal ends, an exterior, and first and second interior portions disposed therewithin;

(b) a light emitter disposed within the first interior portion of the housing;

(c) a light detector disposed within the second interior portion of the housing;

(d) a light transmissive first lens disposed over the light emitter and mounted in the housing between the exterior and the first interior portion of the housing to enable at least portions of light emitted by the light emitter to pass through the first lens from the first interior portion to the exterior;

(e) a light transmissive second lens disposed over the light detector and mounted in the housing between the exterior and the second interior portion of the housing to enable at least portions of light emitted by the light emitter through the first lens and reflecting from oxygenated body fluid adjacent to at least portions of the housing exterior to pass through the second lens from the exterior to the second interior portion, the first and second lenses being separated and spaced apart from one another; and (f) a light barrier positioned between the first interior portion and the second interior portion, the light barrier not permitting light emitted by the light emitter to be transmitted therethrough into the second interior portion for detection by the light detector.

55. The implantable oxygen sensor of claim 54, wherein the light barrier is further positioned between the first lens and the second lens, the light barrier not permitting light emitted by the light emitter to be transmitted therethrough for detection by the light detector.

56. The implantable oxygen sensor of claim 54, wherein the light barrier is one of a membrane and a gasket.

57. The implantable oxygen sensor of claim 54, wherein the light barrier includes one of a membrane and a gasket.

58. The implantable oxygen sensor of claim 54, wherein the light barrier includes at least a portion of the housing.

59. The implantable oxygen sensor of claim 54, wherein the housing is elongated.

60. The implantable oxygen sensor of claim 54, wherein the light barrier includes surfaces configured to guide or reflect light towards the light detector.

61. The implantable oxygen sensor of claim 60, wherein the surfaces are reflective.

62. The implantable oxygen sensor of claim 60, wherein the surfaces are shaped to at least one of collimate and reflect outwardly light emitted by the light emitter.

63. The implantable oxygen sensor of claim 60, wherein the surfaces are shaped to at least one of collimate and reflect outwardly light emitted sideways by the light emitter.

64. The implantable oxygen sensor of claim 60, wherein the surfaces are least one of one of slanted, sloped and parabolically shaped.

65. The implantable oxygen sensor of claim 60, wherein the surfaces are coated with highly reflective material.

66. The implantable oxygen sensor of claim 54, wherein the light barrier includes surfaces configured to guide or reflect light emitted by the light emitter towards the first lens.

67. The implantable oxygen sensor of claim 66, wherein the surfaces are reflective.

68. The implantable oxygen sensor of claim 66, wherein the surfaces are shaped to at least one of collimate and reflect outwardly light emitted by the light emitter.

69. The implantable oxygen sensor of claim 66, wherein the surfaces are shaped to at least one of collimate and reflect outwardly light emitted sideways by the light emitter.

70. The implantable oxygen sensor of claim 66, wherein the surfaces are least one of one of slanted, sloped and parabolically shaped.

71. The implantable oxygen sensor of claim 66, wherein the surfaces are coated with highly reflective material.

72. The implantable oxygen sensor of claim 54, wherein at least portions of the light barrier are formed of silicone.

73. The implantable medical device system of claim 54, wherein at least one of the first and second lenses comprises one of sapphire, ruby and glass.

74. The body implantable medical electrical lead of claim 54, wherein the housing comprises a metal selected from the group consisting of titanium, stainless steel, platinum, niobium, and alloys or combinations thereof.

75. A method of making a body implantable medical electrical lead adapted to be implanted in a living body in operative relation with oxygenated body fluid, the lead comprising a lead body having proximal and distal ends, an electrically insulative material, at least first and second electrical conductors disposed within at least portions of the lead body, the conductors having at least portions of the electrically insulative material disposed therebetween, an oxygen sensor being attached to the lead body and coupled electrically with said first and second lead conductors and comprising a housing having proximal and distal ends, an exterior, and first and second interior portions disposed therewithin, a light emitter disposed within the first interior portion of the housing, a light detector disposed within the second interior portion of the housing, a light transmissive first lens disposed over the light emitter and mounted in the housing between the exterior and the first interior portion of the housing to enable at least portions of light emitted by the light emitter to pass through the first lens from the first interior portion to the exterior, and a light transmissive second lens disposed over the light detector and mounted in the housing between the exterior and the second interior portion of the housing to enable at least portions of light emitted by the light emitter through the first lens and reflecting from oxygenated body fluid adjacent to at least portions of the housing exterior to pass through the second lens from the exterior to the second interior portion, the first and second lenses being separated and spaced apart from one another, and a light barrier positioned between the first interior portion and the second interior portion, the light barrier not permitting light emitted by the light emitter to be transmitted therethrough into the second interior portion for detection by the light detector, the method comprising the steps of:

(a) providing the lead body;

(b) providing the oxygen sensor, and (c) attaching the oxygen sensor to the lead body.

76. The method of claim 75, wherein the method further comprises the step of forming the lead body.

77. The method of claim 75, wherein the method further comprises the step of forming the oxygen sensor.

78. The method of claim 77, wherein the oxygen sensor forming step further comprises the step of including the light barrier between the first and second interior portions.

79. The method of claim 77, wherein the oxygen sensor forming step further comprises the step of including the light barrier between the first and second lenses.

80. A body implantable medical electrical lead adapted to be implanted in a living body in operative relation with oxygenated body fluid, comprising:

(a) a lead body having proximal and distal ends and comprising an electrically insulative material;

(b) at least first and second electrical conductors disposed within at least portions of the lead body, the conductors having at least portions of the electrically insulative material disposed therebetween;

(c) an oxygen sensor attached to the lead body and coupled electrically with said first and second lead conductors, comprising:

(i) a housing having proximal and distal ends, an exterior, and first and second interior portions disposed therewithin;

(ii) a light emitter disposed within the first interior portion of the housing;

(iii) a light detector disposed within the second interior portion of the housing;

(iv) a light transmissive first lens disposed over the light emitter to enable at least portions of light emitted by the light emitter to pass through the first lens from the first interior portion to the exterior, the first lens having an interior surface disposed toward the first interior portion and having an a first index of refraction;

(v) a light transmissive second lens disposed over the light detector to enable at least portions of light emitted by the light emitter and reflecting from oxygenated body fluid adjacent to at least portions of the housing exterior to pass through the second lens from the exterior to the second interior portion and to the light detector, the second lens having an interior surface disposed toward the second interior portion and having a second index of refraction; and (v) a light barrier comprising a coating disposed over at least portions of the interior surface of at least one of the first and second lenses, the coating being one of a high index of refraction coating and an anti-reflective coating, the high index of refraction coating having an index of refraction that is less than the index of refraction of the first or second lens that the high index of refraction coating is disposed over, the anti-reflective coating having an index of refraction that is less than the index of refraction of the first or second lens that the high index of refraction coating is disposed over, whereby light emitted by the light emitter is not refracted or reflected through the first and second lenses into the second interior portion and detected by the light detector.

81. The body implantable medical electrical lead of claim 80, wherein the sensor housing is elongated and tubular, the light transmissive first lens and second lens are formed of first and second portions of a light transmissive, elongated tubular lens element disposed over the light emitter within the first interior portion and the light detector within the second interior portion, respectively, and mounted to the housing between the exterior and first interior portions of the housing such that at least portions of light emitted by the light emitter pass through the first lens from the first interior portion to the exterior and the anti-reflective coating or the high index of refraction coating is applied upon an interior surface portion of the tubular lens element to inhibit reflection or refraction of emitted light through the tubular lens element and into the second interior portion.

82. The body implantable medical electrical lead of claim 81, wherein the first and second lenses are separated and spaced apart from one another and mounted in said housing.

83. The body implantable medical electrical lead of claim 82, wherein the light barrier further comprises light blocking means positioned between the first lens and the second lens for blocking light emitted by the light emitter from being transmitted therethrough for detection by the light detector.

84. The body implantable medical electrical lead of claim 83, wherein the light blocking means is one of a membrane and a gasket.

85. The body implantable medical electrical lead of claim 83, wherein the light blocking means includes one of a membrane and a gasket.

86. The body implantable medical electrical lead of claim 83, wherein the light blocking means includes at least a portion of the housing, and the housing is formed of a material that blocks transmission of light emitted by the light emitter.

87. The body implantable medical electrical lead of claim 83, wherein at least portions of the light blocking means are formed of silicone.

88. The body implantable medical electrical lead of claim 80, wherein the housing is elongated.

89. The body implantable medical electrical lead of claim 80, wherein the at least one lens comprises one of sapphire, ruby and glass.

90. The body implantable medical electrical lead of claim 80, wherein the housing comprises a metal selected from the group consisting of titanium, stainless steel, platinum, niobium, and alloys or combinations thereof.

91. The body implantable medical electrical lead of claim 80, wherein the lead further comprises at least a first electrode for stimulation of cardiac tissue disposed one of near and at the distal end of the lead body.

92. The body implantable medical electrical lead of claim 91, wherein the oxygen sensor attached to the lead body is disposed proximally of the first electrode.

93. The body implantable medical electrical lead of claim 91, wherein the first electrode is a tip electrode.

94. The body implantable medical electrical lead of claim 91, wherein the lead further includes a second electrode.

95. The body implantable medical electrical lead of claim 94, wherein the second electrode is a ring electrode.

* * * * *